United States Patent
Cerwin et al.

(10) Patent No.: US 6,974,415 B2
(45) Date of Patent: Dec. 13, 2005

(54) ELECTROMAGNETIC-ACOUSTIC IMAGING

(75) Inventors: Stephen Anthony Cerwin, Mico, TX (US); David B. Chang, Tustin, CA (US); James E. Drummond, Lincoln City, OR (US); Jane F. Emerson, Irvine, CA (US); Stuart McNaughton, Beaverton, OR (US)

(73) Assignee: Magnetus LLC, Irvine, CA (US)

( * ) Notice: Subject to any disclaimer, the term of this patent is extended or adjusted under 35 U.S.C. 154(b) by 5 days.

(21) Appl. No.: 10/444,202

(22) Filed: May 22, 2003

(65) Prior Publication Data

US 2004/0236217 A1 Nov. 25, 2004

(51) Int. Cl.$^7$ .............................. A61B 8/00; A61B 5/04
(52) U.S. Cl. ...................................... 600/437; 600/407
(58) Field of Search ................................ 600/437, 443, 600/447, 407–412; 73/643

(56) References Cited

U.S. PATENT DOCUMENTS

| | | | |
|---|---|---|---|
| 4,543,959 A | 10/1985 | Sepponen | |
| 5,402,786 A | 4/1995 | Drummond | |
| 5,438,999 A | 8/1995 | Kikuchi et al. | |
| 5,924,986 A | * 7/1999 | Chandler et al. | 600/407 |
| 6,106,463 A | 8/2000 | Wilk | |
| 6,174,284 B1 | 1/2001 | Lillegard et al. | |
| 6,200,267 B1 | 3/2001 | Burke | |
| 6,535,625 B1 | * 3/2003 | Chang et al. | 382/128 |
| 6,645,144 B1 | * 11/2003 | Wen et al. | 600/437 |

FOREIGN PATENT DOCUMENTS

| WO | WO 98/00732 A1 | 1/1998 |
|---|---|---|
| WO | WO 00/22987 A2 | 4/2000 |

OTHER PUBLICATIONS

WO 98/00732 publ. Aug. 1, 1998 Wen.*
"Magnetic Resonance Elastography: Direct Visualization of Propagating Acoustic Strain Waves" by R. Muthupillai et al., Science 269, Sep. 29, 1995.
"An Imaging Method Using the Lorentz Force of a Strong Magnetic Field—Hall Effect Imaging" by Han Wen et al., Proc. Soc. Magn. Reson. Med., Vancouver, B.C., p. 279, May 1997.
"Medical Applications of Microwave Imaging" by L.E. Larson et al., IEEE Press NY, 1985.
"Electrical Impedance Tomography" by J. G. Webster, Ed., Adam Hilger, England and New York, 1990.
"Evaluation of Impedance Technique for Detecting Breast Carcinoma Using a 2D Numerical Model of the Torso" by Radai M. M., Abboud S., Rosenfeld M. Ann. NY Accad Sci 1999 Apr. 20; 873:360–9.

(Continued)

Primary Examiner—Francis J. Jaworski
(74) Attorney, Agent, or Firm—MacPherson Kwok Chen & Heid LLP; Tom Chen

(57) ABSTRACT

Ultrasound induced by RF irradiation within FDA exposure limits is produced with sufficient signal-to-noise ratio to allow acquisition of sub-millimeter resolution images within practical time frames.

23 Claims, 6 Drawing Sheets

OTHER PUBLICATIONS

"Inverse Boundary Value Problem" by Margaret Cheney, Am. Scientist 1997 85 pp. 448–455.

"Magnetic Impedance Tomography" by Tozer J.C., Ireland R.H., Barber D.C., Barker A.T., Ann. NY Acad. Sci. 1999; Apr. 20; 873–353–9.

"Classical Electricity and Magnetism" by Wolfgang K.H. Panofsky and Melba Philips, Reading, Mass., Addison Wesley Publishing Company, Inc. (1956) p. 162.

"Application of Electrical Impedance Analysis for Diagnosis of a Pulmonary Mass" by S. Kimura et al., Chest 105(6), 1679 (1994).

"Impedance Spectra of Tumour tissue in Comparison With Normal Tissue; A Possible Clinical Application for Electrical Impedance Tomography" by B. Blad et al., Physiological Measurement 17, A105 (1996).

"New Imaging Techniques Detect Diminutive Danger Signs" by William Leventon, Medical Devices & Diagnostic Industry, 48 (Oct., 2000).

"Biochemistry" by J.W. Woodbury et al., Chapter 11 in *Physical Chemistry, An Advanced Treatise*, ed. Henry Eyring, New York: Academic Press (1970).

*Diagnostic Ultrasound: Principles, Instruments and Exercises*, by Frederick W. Kremkau, Philadelphia: W.B. Saunders Co., 34 (1989).

* cited by examiner

ELECTROMAGNETIC-ACOUSTIC IMAGING

BACKGROUND

1. Field of the Invention

The present invention relates to medical diagnostic equipment, and more particularly to medical diagnostic equipment using radio-frequency (RF) fields, ultrasonic detectors and signal processors, to produce visual images and digital outputs.

2. Description of Related Art

Radio frequency (RF) electromagnetic (EM) fields are widely used for medical diagnostics in magnetic resonance imaging (MRI). In MRI, RF is used to excite coherent precession of nuclear magnetic moments in a strong static background magnetic field. Precessing moments provide imaging information through the subsequent RF fields that they generate. These subsequent fields depend on the local densities of moments, their relaxation times, and precession frequencies, which in turn depend upon the local chemical and physical environment of the precessing nuclei. Detection of the subsequent fields has provided images of molecular properties with good spatial resolution (to several micrometers). An imaging apparatus which relies on conventional MRI is expensive, bulky, lacks portability, and is associated with high facility costs because of the shielding and cryogenic requirements for strong magnetic fields.

Ultrasound, which usually produces images with millimeter resolution based on acoustic impedance differences between organs, has been used extensively for imaging in both medical and non-medical applications. Medical applications of ultrasound include imaging and flow measurements. Conventional ultrasound scanners are relatively inexpensive compared to MRI and have the advantage of portability.

Ultrasound has been used in conjunction with MRI to characterize the structure and quality of tissue imaged by magnetic resonance. MRI has also been used to sense organ motion produced by sound waves transmitted into the patient which gives a measure of the elasticity of tissues observed.

Another approach to diagnostic imaging requires application of electrical voltage to electrodes on the patient in a very strong steady magnetic field. Images are formed by detection of the resulting ultrasound. Alternatively, intense ultrasound is transmitted and the resulting voltages on the electrodes detected to form an image.

Microwave EM imaging without magnetic resonance has been considered for medical diagnostics. Excellent image contrast is produced because of the large variation of microwave EM refractive index among soft body tissues. However these large variations deflect the paths of the microwaves traversing the body and thus distort the image produced. This effect also causes variable concentrations of microwave power deposition in organs.

Direct application of electrical currents to the patient with observation of resulting voltages has been studied as an imaging method. Development and applications of these methods are motivated by the findings that malignant (cancerous) tissue may be differentiated from benign tissue by electrical conductivity. For example, breast cancer tumors have been reported to have electrical conductivity twenty to fifty times that of normal surrounding tissue. However, imaging of tissue conductivity from such measurements involves inverting an elliptic differential equation, which smoothes out source details at distant observation points. This process is unstable in the sense that a small change (e.g. due to noise or interference) in the received observational data produces large changes in the computed image.

In lieu of the application of electrodes to the body, alternating magnetic fields have been used to produce images from currents in a phantom and a human thorax during respiration. A problem with magnetic detection at sub-microwave frequencies is its inherently low resolution.

Other innovations recently introduced require such extensive data collection and processing that it must be done offline, taking significantly longer than the patient scan.

SUMMARY

The present invention includes methods of imaging techniques and embodiments for an imaging apparatus based on the principles of electromagnetic induced ultrasound imaging.

Electromagnetic acoustic imaging (EMAI) is a technique in which an RF electric field is created in the object of interest by irradiation with electromagnetic coils, directly via electrodes in the vicinity or on the surface, or by inserted electrodes. Mechanical stresses associated with the electric fields in interior deformable regions generate ultrasound waves. The net stresses are largest at interfaces between regions exhibiting the largest conductivity changes. The ultrasound can be detected and spatially localized with conventional ultrasound scanning and focusing detection systems to produce an image which depends on electrical conductivity and acoustic properties. Pulsed, chirped, and Fourier transform tomographic imaging approaches are possible.

For medical applications, EMAI offers diagnostic utility because electrical conductivity differences are large between tissue types and disease states. For example, it has been shown that conductivity values for malignant (cancerous) lesions may be 50 fold higher than those for benign lesions. As a result, the ultrasound generated at a target site by the electrical stresses at the interfaces provides an effective means of imaging the boundaries between different types of normal tissues and the boundaries between normal and cancerous tissues. When used as an adjunct to conventional ultrasound imaging of tissue acoustic parameters, the proposed ultrasound imaging of tissue conductivity properties is especially convenient, because of the ease of co-registration of the two types of images. Medical applications for this technique include, but are not limited to: characterizing lesions in the breast, thyroid, prostate or other pelvic regions as benign or malignant; volume measurements of fluid spaces such as cysts, abdominal cavity, heart, and blood vessels; and flow measurement in blood vessels.

The generalized apparatus includes a pulsed RF generator driving current through one or more induction coils, adjacent support for a patient, one or more ultrasonic sensors located on or near the patient's skin, and a means for signal processing and storage. In a simplified embodiment, such means may consist of a small standard four-channel, digital oscilloscope, and a pre-programmed laptop computer. The method includes applying short pulses of RF current to the coil(s), and collecting, recording and processing ultrasonic signals produced by interaction of the resulting E fields with discontinuities and gradients of conductivity in a body. The outputs of the apparatus may be a viewable presentation of tomographic slices from a variety of angles and depths and precise values of 3D Cartesian coordinates of conduction anomalies, along with indications of their sizes and shapes.

In one aspect of the present invention a method is provided for locating conductivity gradients and discontinuities within a subject. The method includes impinging a target site including conductivity gradients and discontinuities within a subject with pulsed RF electric fields. The method further includes receiving ultrasound signals produced at the target site caused by the impinging of the target site with the pulsed RF electric fields and processing the ultrasound signals to quantitatively locate features of the conductivity gradients and discontinuities defined at the target site.

In another aspect of the present invention, an apparatus is provided for locating conductivity gradients and discontinuities within a subject. The apparatus includes a means for impinging a target site including conductivity gradients and discontinuities within a subject with pulsed RF electric fields. A means is also included for receiving ultrasound signals produced at the target site caused by the impinging of the target site with the pulsed RF electric fields. The apparatus further includes a means for processing the ultrasound signals to quantitatively locate a feature of the conductivity gradients and discontinuities defined at the target site.

In yet another aspect of the invention, a method is provided for locating conductivity gradients and discontinuities within a subject, which includes impinging a target site including conductivity gradients and discontinuities within a subject with pulsed RF electric fields; sensing ultrasound pulse signals produced at a plurality of ultrasound sensors within acoustic range of the target site caused by the impinging of the target site with the pulsed RF electric fields using a plurality of sensor sources and including electromagnetically sensing the pulsed RF fields as a time reference signal; and computing time delays of the recorded arrival times from the coordinates of one to a plurality of the conductivity gradients and discontinuities using the time reference signal; assigning each of the plurality of sensor sources of the ultrasound pulse signals arbitrarily among sources compatible with any of the measured time delays and the ultrasound signals; calculating all the measured transit times with the assignments; comparing the calculations with all the transit times; and changing the assignments until the calculated and measured transit times agree within a longitudinal resolution interval.

In yet another aspect of the invention, a method is provided for detecting conductivity gradients and discontinuities within a subject including generating an ultrasound image of a target site within a subject; generating an electromagnetic acoustic image; and combining the ultrasound image and the electromagnetic acoustic image to create a first diagnostic image.

Imaging from ultrasound generated by electromagnetically induced RF ohmic currents offers considerable advantages, in cost, size, and the provision of complementary information, while avoiding the limitations inherent in other approaches.

When compared to Resonant RF MRI, the present invention does not require a static background magnetic field. Consequently, the size and cost of the equipment may only be a fraction of that for an MRI scanner. The information provided by the present invention is complementary to that provided by MRI. For example, the information includes local tissue conductivity variations rather than relaxation time and resonance frequency. Moreover, the present invention can be used during surgical procedures. Further, MRI parameters typically vary by less than a factor of 2 between different soft tissues, the electrical conductivity imaged by the proposed technique can vary by factors much greater than 2.

When compared to Ultrasound, the present invention can obtain excellent contrast because it measures the large intrinsic electrical conductivity differences between tissue types and between abnormal and normal tissue (e.g., 4000%, see Table I). The 40-fold difference in intrinsic tissue electrical conductivity should constitute a considerable advantage for contrast. The present invention does not require the use of intense ultrasound waves. Better resolution is expected since the ultrasound does not need to travel two ways (from a transducer to the tissue and back to the detector), but only from the tissue to the detector. At the same time, complementary information is provided (electrical vs. direct mechanical properties), so that consideration is given to using both compact and low cost approaches to more fully characterize the organs of interest. When this is done, it is especially straightforward to co-register the images of electrical conductivity variations with the conventional images of tissue acoustic properties.

When compared with non-resonant RF, the present invention capitalizes on the large intrinsic contrast of tissues due to the 4000% variation in electrical properties among different tissues, but avoids the resolution limitations imposed by the long wavelengths of the RF electromagnetic waves. Good resolution can be achieved by using the shorter wavelength ultrasound waves for imaging the conductivity changes.

When compared with RF current tomography, the present invention capitalizes on the large intrinsic contrast of tissues due to the 4000% variation in electrical properties among different tissues, but avoids the poor resolution imposed by the fact that the currents satisfy Laplace's equation rather than a wave equation. The present invention does not require any direct electrical electrode contact with the patient (although direct electrode contact is an option). Good resolution is achieved by imaging with the short wavelength ultrasound waves generated by the electric fields (five orders of magnitude shorter than the illuminating RF). The most direct way of obtaining good images is with acoustic lensing (although tomographic methods can also be used with the shorter wavelength ultrasound waves).

When compared with Hall-effect imaging, the present invention does not require any electrical electrode contact with the patient (although it is possible to apply the internal electric fields with this option). No intense ultrasound pulse or large expensive background magnetic field is required. Improved contrast is expected due to larger signal-to-noise ratio resulting from fast signal averaging and discrimination of ultrasound signals, at twice the excitation frequency, from the EM excitation. Moreover, there is no requirement for offline processing because acoustic lens focusing has replaced the electronic focusing. There is also an availability of portable embodiments.

DETAILED DESCRIPTION

In electromagnetic acoustic imaging (EMAI), image contrast depends on the spatial variation of electrical conductivity which is diagnostically useful and in particular, has been shown to be significant in distinguishing malignant from benign lesions. The present invention provides detectable ultrasound produced by electric fields in an environment containing one or more compressible regions of electrical conductivity gradient or discontinuity. The electric fields may be effectively produced by electromagnetic irradiation in the radio frequencies. The induced ultrasound has sufficient signal-to-noise ratio (SNR) to allow for the generation of diagnostically useful images in practical time frames.

Figure 1:
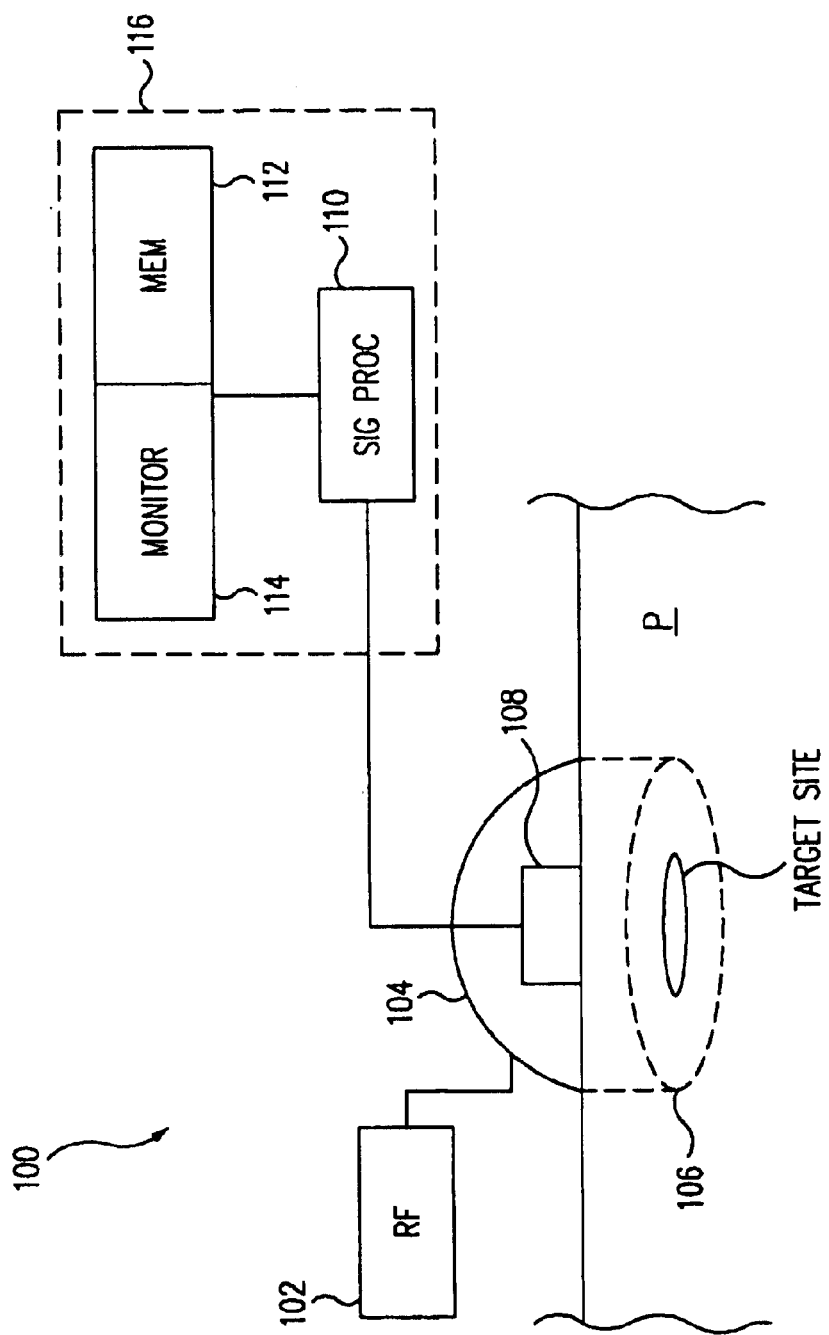
FIG. 1 is a simplified illustration of an EMAI system in accordance with principles of the present invention.

FIG. 1 is a simplified illustration of the generalized EMAI system 100, which includes a pulsed RF generator 102 used to drive current through one or more induction devices 104, to form an E field 106, which is made to impinge on a target site. System 100 also can include one or more ultrasonic sensors 108 located on or near the patient's skin P to be in acoustic range of an ultrasound signal emanating from the target site. The ultrasound signal is processed using a means for signal processing 110, which generates data, which may be stored in a memory 112 and viewed on a monitor 114. In one embodiment, signal processing means 110, memory 112 and monitor 114 may be all encompassed in an apparatus 116, which includes a small standard four-channel, digital oscilloscope, and a pre-programmed laptop computer. The outputs of the apparatus may be a viewable presentation of tomographic slices from a variety of angles and depths and precise values of 3D Cartesian coordinates of conduction anomalies, along with indications of their sizes and shapes.

Figure 6:
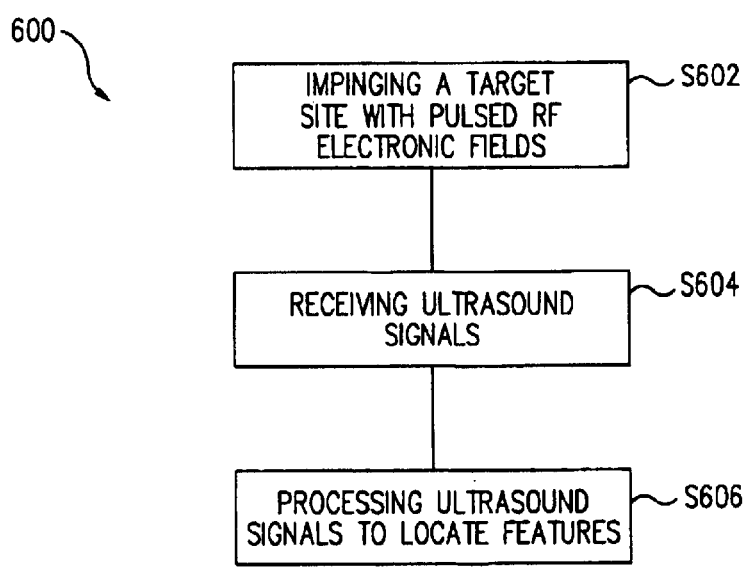
FIG. 6 is a flow diagram illustrating an embodiment in accordance with principles of the present invention.

FIG. 6 is a flow diagram including an EMAI method or process 600 for imaging a patient. Method 600 can include impinging a target site, which includes conductivity gradients and discontinuities within a subject with pulsed RF electric fields (S602). As described in greater detail below, the pulsed RF electric fields cause ultrasound pulse signals to be produced by interaction of the resulting E fields with the discontinuities and gradients of conductivity in the tissue of the subject. The ultrasound pulse signals are sensed using one to a plurality of ultrasound sensors within acoustic range of the target site (S604). In one embodiment, the ultrasound pulse signals can be electromagnetically sensed as a time reference signal. Method 600 also includes processing the ultrasound signals (S606), which includes various procedures. For example, processing may include computing time delays of the recorded arrival times from the coordinates of one to a plurality of the conductivity gradients and discontinuities using the time reference signal and assigning each of the plurality of sensor sources of the ultrasound pulse signals arbitrarily among sources compatible with any of the measured time delays of said ultrasound signals. All measured transit times are calculated using the assignments and the calculations are compared with all of the transit times. The assignments can be changed until the calculated and measured transit times agree within a longitudinal resolution interval.

A1. Supporting Physics

The magnitude of the ultrasound generated by the applied electromagnetic stresses can be estimated by considering a body with isotropic properties in which there is a spatially varying electrical conductivity.

Equations of Motion

The starting point is the following set of four equations: the generalized Ohm's law, momentum equation, continuity equation, and constitutive equation relating pressure to density, in their lowest approximation:

Generalized Ohm's law: $j = \sigma(E+(V) \times B)$       A(1)

Momentum equation: $\rho dV/dt = -\nabla P + j \times B + \rho_q E$      A(2)

Continuity equation: $\partial \rho / \partial t + \nabla \cdot (\rho V) = 0$      A(3)

Pressure equation: $P = \rho V_s^2$      A(4)

Here, j denotes the current density, $\rho_q$ is the charge density, $\sigma$ is the conductivity, E and B are the electric and magnetic fields, $\rho$ is the mass density, P is the acoustic pressure, $V_s$ is the speed of sound, and V is the mass velocity. In Eq. A(4), the pressure and density are to be regarded as the perturbations from the background quantities.

For generality, B is considered to consist of a static portion $B_0$ and an RF portion $B_{RF}$ oscillating with an angular frequency $\omega$. Alternatively, below, B shall be considered without the static portion.

These equations apply when the frequency is less than the plasma and collision frequencies and the Debye shielding length is less than any spatial variation of interest, for under those circumstances charge neutrality is satisfied unless there is a spatial variation in the dielectric constant or conductivity. These conditions are well satisfied for the imaging applications of interest, since in body electrolytes, typical plasma and collision frequencies are of the order of $10^{12}$ Hz and the typical shielding distance, 4.5 $\mu$m, is almost as small as inter-particle spacings.

The acoustic wave equation for the ultrasound can be obtained by combining Eqs. A(1)–A(4):

$$\nabla^2 P - \frac{1}{V_s^2} \frac{\partial^2 P}{\partial t^2} = \nabla \cdot [j \times B + \rho_q E] \quad\quad A(5)$$

The right hand side of equation A(5) consists of the source terms, and shows that the ultrasound is generated by variations in the ohmic currents and charge densities. Both of these source terms give information on the spatial variation of the conductivity, since both the current density and charge density depend on the conductivity. Variations in the conductivity will reflect changes in ionic concentration, viscosity, and the volume fraction available for current flow. The latter two are related, as effective viscosity will depend on the presence of obstructions to fluid flow.

Specifically, the current density and charge density can be expressed approximately in terms of the electric field as follows:

$j => \sigma E$      A(6)

$\nabla \cdot [\in E] = \rho_q$      A(7)

Equation A(6) is an approximation to Eq. A(1), resulting from bulk velocity, V<1 m/s, and magnetic field, B<0.1 tesla, V×B<0.1 volt/m. Equation A(7) is Poisson's equation.

In a conducting medium, the effective dielectric constant $\in$ comprises both the true dielectric constant $\in_q$ and the contribution of the conductivity:

$$\in = \in_q + \sigma/i\omega \qquad \text{A(8)}$$

On inserting Eqs. A(6)–A(8) into Eq. A(5), the result is:

$$\nabla^2 P - \frac{1}{V_s^2}\frac{\partial^2 P}{\partial t^2} = \nabla \cdot [\sigma E \times B + \nabla \cdot \{(\varepsilon_q + \sigma/i\omega)E\}E] \qquad \text{A(9)}$$

As shown later, for the parameters of interest in the body, $$\in_q << \sigma/i\omega \qquad \text{A(10)}$$

Accordingly, in the body, the ultrasound generated by the RF electromagnetic fields is directly proportional to the spatial variation of the electrical conductivity.

Stress Tensor

It is also possible to express the physics of Eq. A(9) in terms of the mechanical stress generated by the electromagnetic fields. For some applications, this alternative formulation can be more useful. The stress tensor from an electromagnetic field in a medium has been derived in several places. The stress tensor $T_{\alpha\beta}$ for the electromagnetic field in a medium of arbitrary dielectric constant:

$$T_{\alpha\beta} = \in_0 \kappa \qquad \text{A(11)}$$

and arbitrary magnetic permeability:

$$\mu = \mu_0 \kappa_M \qquad \text{A(12)}$$

is:

$$T_{\alpha\beta} = E_\alpha D_\beta - (\tfrac{1}{2})\delta_{\alpha\beta}E_\gamma D_\gamma + H_\alpha B_\beta - (\tfrac{1}{2})\delta_{\alpha\beta}H_\gamma B_\gamma \qquad \text{A(13)}$$

where the Einstein summation convention is used for repeated indices and the indices run over the space coordinates from 1 to 3, and where:

$$\in_0 = (36\pi 10^9)^{-1} \text{ farad/meter} \qquad \text{A(14)}$$

and $\mu_0 = 4\pi 10^{-7}$ henry/meter. Here, the electric displacement $D_\alpha$ is related to the electric field intensity $E_\alpha$ by:

$$D_\alpha = \in E_\alpha = \in_0 \kappa E_\alpha \qquad \text{A(15)}$$

and the magnetic flux density $B_\alpha$ is related to the magnetic field intensity $H_\alpha$ by:

$$B_\alpha = \mu H_\alpha = \mu_0 \kappa_M H_\alpha \qquad \text{A(16)}$$

The stress tensor $T_{\alpha\beta}$ has the usual definition: the electromagnetic force in the αth direction on a surface area with the components $dS_\beta$ given by:

$$F_\alpha = T_{\alpha\beta} dS_\beta \qquad \text{A(17)}$$

Panofsky and Phillips demonstrate that the per unit volume force in the αth direction due to the electromagnetic field is:

$$f_\alpha = \partial T_{\alpha\beta}/\partial x_\beta \qquad \text{A(18)}$$

and that:

$$\partial T_{\alpha\beta}/\partial x_\beta = \rho_{True}E - (\in_0 E^2/2)\nabla \kappa - (\mu_0 H^2/2)\nabla \kappa_M + j_{True} \times B + \partial/\partial t [D \times B] \qquad \text{A(19)}$$

In the body, $j_{True}$, is combined with $\partial D/\partial t$ writing:

$$\kappa = \kappa_{dielectric} - i\sigma/\omega \in_0 \qquad \text{A(20)}$$

$$\kappa_M = \text{constant} \qquad \text{A(21)}$$

where any variation in the magnetic permeability through the body is ignored, and accommodate conduction in an effective dielectric constant is accommodated:

For the frequencies of interest, and for electrolytes in the body, it can be shown that $\kappa_{dielectric}$ can be ignored compared with $i\sigma/\omega \in_0$:

$$\kappa_{dielectric} = O(80) \qquad \text{A(22)}$$

$$\sigma = O(0.5 \text{ siemens/meter}) \qquad \text{A(23)}$$

and for an angular RF frequency as large as, $$\omega = O(10^7 \text{ sec}^{-1}). \qquad \text{A(24)}$$

Then $$\sigma/\in_0 \omega \kappa_{dielectric} = O[700] = >>1, \text{ and } \kappa \approx i\sigma/\omega \in_0. \qquad \text{A(25)}$$

In that case it is recognized that the $[(\partial D/\partial t) \times B]$ portion of the $\partial/\partial t$ $[D \times B]$ term in Eq. A(19) as the per unit volume $j \times B$ force in Eq. A(2). The remaining terms describe the $\rho_q E$ term in Eq. A(2). The $E_\alpha D_\beta - (\tfrac{1}{2})\delta_{\alpha\beta}E_\gamma D_\gamma$ terms in the stress tensor $T_{\alpha\beta}$ describe the effect of the $\rho_q E$ source term in Eq. A(2) on a surface: specifically it describes the stress due to surface charges induced at interfaces.

Spherical Regions of Interest

The following embodiment is a calculation of the ultrasonic waves that can be produced by an RF electrical field in and around a region with dimensions on the order of a cubic millimeter which has conductivity much greater than the surrounding region. In this example, the region is taken to be a uniform sphere.

The response at r, θ, φ to a source of forced motion at R, Θ, Φ, is given by a Green's function, which may be expressed as a series of spherical harmonics and associated radial functions. Most of these have angular dependence, which produces multipolar acoustic motion decaying as $(1/r)^x$ with $x \geq 2$. Only one of these carries non-zero, finite energy density to the center of the inner sphere while connecting to the reciprocal of distance to the first power radiation, $$y_0(kr) = A \cos(kr)/kr \text{ where } k = 2\omega/V_S \qquad \text{A(26)}$$

where $V_S$ is the speed of sound. The inner solution, $y_0(kr)$, of the equation for sound propagation is attached to an outer, radiating solution, $$H(kr) = C(kR)e^{(ikr)}/kr \qquad \text{A(27)}$$

At r=R, the radius of the ROI, there will be a discontinuity due to the average input stress, T at 2ω (only the angular average is important because angular variations die off more rapidly with r):

$$A \cos(kR)/kR - C(kR)e^{(ikR)}/kR = T_{Max} \qquad \text{A(28)}$$

The average radial velocity of tissue in the ultrasound field is continuous at r=R, requiring that the radial derivative $y_0(kr)$ match that of H(kr) there:

$$-A \sin(kR)/kR - A \cos(kR)/(kR)^2 = iC(kR)e^{(ikR)}/kR - C(kR)e^{(ikR)}/(kR)^2 \qquad \text{A(29)}$$

The solution of these simultaneous equations for the radiated pressure wave amplitude is $$C(kR) = TN(kR)/D(kR) \qquad A(30)$$

where $$N(kR) = kR \cdot (-ikR)e^{2ikR} + (ikR) + e^{2ikR} + 1 \qquad A(31)$$

and $$D(kr) = (2kR)e^{2ikR} - 2i(kR)^2 e^{2ikR} + (ikR)e^{3ikR} - (ikR)e^{ikR} - e^{3ikR} - e^{ikR} A(32)$$

Figure 5:
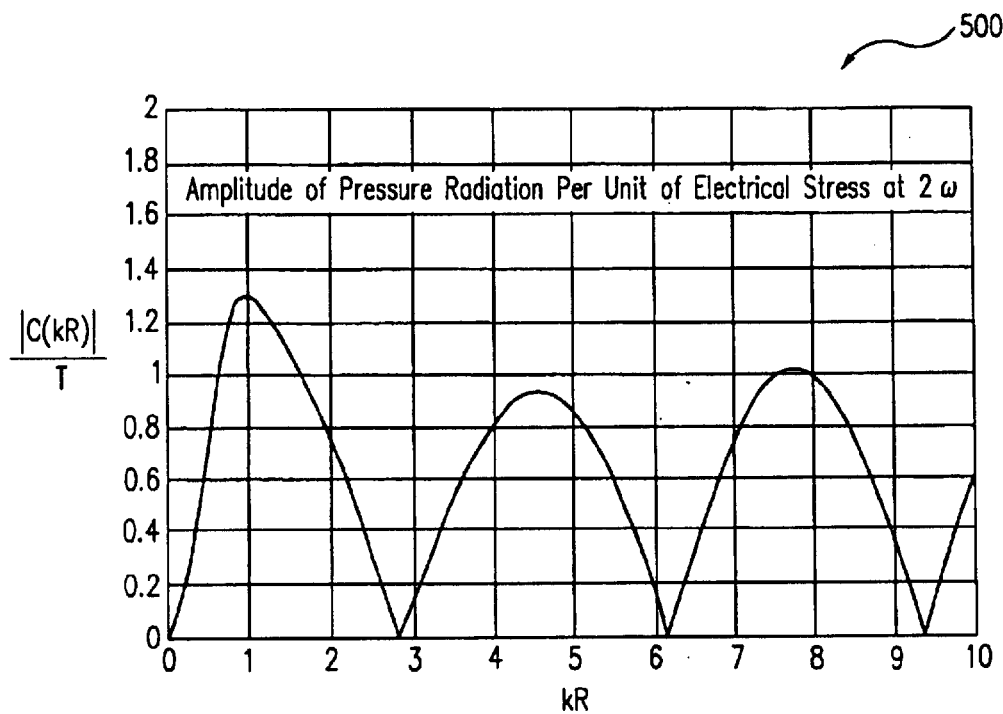
FIG. 5 shows an exemplary ultrasonic radiation amplitude |C(kR)| from a 1 mm diameter region of spatially varying conductivity subject to electrical stress, $T = \in E^2/2$, as a function of region-of-interest (ROI) radius times wave number of ultrasound, _kR, which arises from the applied E field in accordance with an embodiment of the present invention.

FIG. 5 is a plot 500 of $|C(kR)|/T$ from Eq. A(30) where, for applications in breast imaging, $V_S$ is taken to be the speed of sound in breast fat, $V_S = 1440$ m/s. This shows a small resonance at $kR = 0.9$ which could provide a measurement for R by adjusting $\omega$.

The acoustic wave equation of Eq. A(9) is the physics basis for electromagnetic acoustic imaging. Numbers inserted into this equation demonstrate that in the body, the ultrasound generated by RF electromagnetic fields provides a high resolution image of the spatial variation of the body's electrical conductivity.

The source terms in the acoustic wave equation, Eq. A(9), are rewritten in terms of the spatial variation of dielectric constant and electrical conductivity in Eq. A(19). The latter equation is derived from the stress tensor of Eq. A(13), which expresses the stress generated by electric and magnetic fields in a medium. For RF electromagnetic fields in the body, the electrical conductivity terms dominate in the stress tensor expressions, again showing that the associated ultrasound generated by the RF electromagnetic fields provides a picture of the spatial variation of the body's electrical conductivity.

A2. Electrical Conductivity Variation in the Body

In the foregoing, it is shown that the proposed technique provides a high contrast image of the body's normal and diseased components because of the large variation of the electrical conductivity between different tissues and between normal and diseased tissues. In support thereof, typical values for this conductivity variation are presented.

Tissue Variation

Conductivities vary considerably from tissue to tissue. One MHz data taken from "Compilation of the Dielectric Properties of Body Tissues at RF and Microwave Frequencies" (including a 40 year literature search) by Camelia Gabriel, PhD., Sami Gabriel, MSc, Physics Department, King's College London, London WC2R2LS,UK are presented below in Table 1.

TABLE 1

| Tissue | Relative Permittivity $\epsilon_r$ | Conductivity (S/m) $\sigma$ | Combination $\sigma - \omega\epsilon_0\epsilon_r i$ |
|---|---|---|---|
| Blood | 3.8E3 | 1.3E0 | 1.3 − 0.2i |
| Grey matter | 1E3 | 2.5E−1 | 0.25 − 0.0256i |
| White matter | 6E2 | 1.3E−1 | 0.13 − 0.033i |
| Heart | 2.0E3 | 3.8E−1 | 0.38 − 0.1i |
| Kidney | 2.0E3 | 2.0E−1 | 0.2 − 0.1i |
| Liver | 1.8E3 | 2.0E−1 | 0.2 − 0.1i |
| Lung (inflated) | 7.0E2 | 1.2E−1 | 0.12 − 0.039i |
| Spleen | 2.0E3 | 1.9E−1 | 0.19 − 0.11i |
| Uterus | 2.0E3 | 5.0E−1 | 0.5 − 0.11i |
| Muscle (transverse) | 1.8E3 | 6.0E−1 | 0.6 − 0.1i |
| Muscle (longitudinal) | 5.0E2 | 6.0E−1 | 0.6 − 0.28i |
| Skin (wet) | 2.5E3 | 2.9E−1 | 0.29 − 0.014i |
| Aorta | 3.5E2 | 3.3E−1 | 0.33 − 0.019i |

TABLE 1-continued

| Tissue | Relative Permittivity $\epsilon_r$ | Conductivity (S/m) $\sigma$ | Combination $\sigma - \omega\epsilon_0\epsilon_r i$ |
|---|---|---|---|
| Bone cancellous | 5.5E2 | 8.5E−1 | 0.85 − 0.031i |
| Bone cortical | 1.5E2 | 3.0E−2 | 0.03 − 0.0083i |
| Cervix | 4.5E2 | 5.3E−1 | 0.53 − 0.025i |
| Breast fat | 1.8E1 | 1.8E−2 | 0.018 − 0.001i |
| Breast cancer | | 3.6–7.2E−1 | ** |
| Thyroid | 2.8E3 | 5.0E−1 | 0.5 − 0.16i |
| Testis | 3.2E3 | 6.0E−1 | 0.6 − 0.18i |
| Ovary | 1.7E3 | 2.9E−1 | 0.29 − 0.95i |
| Bladder | 5.7E2 | 2.1E−1 | 0.21 − 0.032i |

Supported by Armstrong Laboratory (AFMC), Occupational and Environmental Health Directorate, Radio frequency Radiation Division 2503 D Drive Brooks Air Force Base TX, 78235-5102 AL/OE-TR-1996-0037 updated 8 Jan. 1999. Legal Documentation http://brooks.af.mil/AFRL/HED/hedr/reports/dielectric/Report.htm Contacts at Brooks Air Force Base, William Hurt, MSc., Patrick Mason, PhD.
**http://www.imaginis.com/t-scan/how-work.asp.

Variation Between Normal and Cancerous Tissue

In addition, it has been reported that the conductivity in breast cancer is twenty to fifty times as high as in the surrounding normal tissue. The conductivity and capacitance in cancerous tissue have been cited as being 50 times that in normal tissue.

As will be seen in the numerical examples below, midrange values of the differences are adequate to give striking contrasts in the ultrasound images induced by RF electromagnetic fields.

Significance and Frequency Limitations of Conductivity Measurements

The ohmic currents in tissue flow primarily in the intracellular space contained by cellular membranes, or in the extracellular space comprised of blood vessels and the interstitial space (the portion directly in contact with the cells). In muscle tissue, for instance, 85–90% of the total volume is occupied by muscle cells and about half of the remaining 10–15% extracellular volume by blood vessels. The composition of the electrolytes in these spaces varies, but both intracellular and extracellular electrolytes have concentrations of the order of 300 micromoles per cm$^3$. Na$^+$ and Cl$^-$ are the dominant ions in interstitial fluid, and K$^+$ and organic anions with average valences of 2.1 are the dominant ions in intracellular fluid. A typical value for resistivity is 100 ohm cm.

The cell walls are comprised of membranes with typical thickness of 50–100 Angstroms and surface capacitance on the order of a microfarad per cm$^2$. In addition, the cells contain several membrane structures, e.g. endoplasmic reticulum and mitochondria. The fraction of intracellular volume occupied by these structures is small. Although cell sizes vary markedly, a typical dimension is of the order of 100 microns.

The foregoing information sets a lower limit on the RF frequency that can be used for generating ultrasound from induced ohmic currents. The desired condition is that the admittance associated with the electrolyte conductivity should be less than that due to membrane capacitance. Then the induced voltage will be available primarily to drive the ohmic currents. This condition may be written roughly as:

$$Y_E/Y_M = \sigma_e/(\omega C_M d) < 1 \qquad A(33)$$

where $Y_M$ is the admittance of unit area of the membrane capacitance, $Y_E$ is the admittance of unit area of the electrolyte, $\omega$ is the angular frequency of the RF, $C_M$ is the membrane capacitance per unit area, $\sigma_e$ is the conductivity of the electrolyte, and d is a typical dimension of an ohmic path—which is taken to be a typical dimension of a cell, $\approx 10^{-4}$ m. For the numbers cited above, this sets as the lower limit on angular frequency:

$$\omega > 10^6 \text{ sec}^{-1}$$

With acoustic velocities of $1.5 \times 10^5$ cm/sec, the corresponding acoustic wavelengths are less than 1 cm. (A 1 mm wavelength corresponds to a frequency of 1.5 MHz.). Since features of this size or smaller are of interest, the frequency limitation is not a hindrance.

The effective local conductivity is a weighted average of that due to the electrolytes in the extracellular and intracellular spaces. The law of mixtures can be used to determine the weighting (e.g. the Maxwell-Wagner relation, or the heuristic Bruggerman relation.)

The electrical conductivity which the proposed technique measures with ultrasound, is directly proportional to ionic concentration, and inversely proportional to the electrolyte viscosity and effective ion radius. The viscosity, $\eta$, is related to the water diffusion coefficient $D_{water}$ by $$D_{water} = \eta/\rho_0 \text{ with } \rho_0 \text{ the ambient mass density.} \qquad \text{A(34)}$$

Thus, variation in tissue conductivity should reflect variation in all these quantities, as well as in the free volume for electrolytes.

The body's electrical conductivity varies by several hundred percent from organ to organ and from normal tissue to cancerous tissue. The conductivity variation is due to variation in the free volume available for electrolytes, and to the variation in viscous drag in the different tissues. The present invention gives information on the conductivity variation as long as the RF angular frequencies are greater than $10^6$ sec$^{-1}$.

A3. Comparison of Mechanisms for EM-Induced Ultrasound

Below is detailed the relative contribution to the ultrasound signal of the two source terms, $j \times B$ and $\rho_q E$. It will be shown that for typical RF frequencies in the body, the contribution from $\rho_q E$ dominates. This is desirable, since it means that the proposed technique does not require an (expensive) large and uniform background magnetic field.

Generation of Ultrasound from $j \times B$

Including only this source term in Eq. A(9), the basic equation for the $j \times B$ generation of ultrasound is:

$$\nabla^2 P - V_s^{-2} \partial^2 P / \partial t^2 = \nabla \cdot [\sigma E \times B], \qquad \text{A(35)}$$

which shows that the ultrasound generated by the ohmic currents gives information on the spatial variation of the conductivity. Denoting the angular frequency of the ultrasound by $\Omega$, Eq. A(35) becomes a Helmholtz equation $$\nabla^2 P + k^2 P = \nabla \cdot [\sigma E \times B] \qquad \text{A(36)}$$

where the acoustic wavenumber k is given by $$k^2 = \Omega^2 / V_s^2 \qquad \text{A(37)}$$

with $V_s$ denoting the speed of sound.

To understand the information provided by P, consider the solution in the far (radiation) zone at a distance R from the source region where $k \cdot R \gg 1$ and the dimension of the source region is much less than R. The solution then to Eq A(36) is:

$$P(k,R) = (\tfrac{1}{4}\pi)(\exp(ikR)/R) \int d^3 r \exp(ik \cdot r) \nabla \cdot [\sigma E \times B] \qquad \text{A(38)}$$

where k is the wavevector from the source region to the detector, and the position vector r is integrated over the source region. As shown in the above referenced patent application, Eq. A(38) was integrated by parts, yielding:

$$P(k,R) = -i(\exp(ikR)/R)(\tfrac{1}{4}\pi) \int d^3 r \exp(ik \cdot r) \sigma(r)(E \times B) \cdot k \qquad \text{A(39)}$$

In that approach, E is provided by an RF coil, and B could either be provided by the same coil or by a background magnet or DC coil.

Instead:

$$\nabla \cdot [\sigma E \times B] = B \cdot (\nabla \times \sigma E) - \sigma E \cdot (\nabla \times B) \qquad [\text{A(40)}]$$

Maxwell's equations, $$\nabla \times B = (\mu \in) \partial E / \partial t + \mu \sigma E \qquad \text{A(41)}$$

$$\nabla \times E = -\partial B / \partial t \qquad \text{A(42)}$$

can be used to rewrite Eq. A(40) as:

$$\nabla \cdot [\sigma E \times B] = B \cdot [-(\sigma) \partial B / \partial t + \nabla \sigma \times E] - \qquad \text{A(43)}$$

$$\sigma E \cdot [(\mu \varepsilon) \partial E / \partial t + \mu \sigma E]$$

$$= -(\sigma/2) \partial / \partial t \{\mu \in E^2 + B^2\} + \qquad \text{A(44)}$$

$$B \cdot \nabla \sigma \times E - \mu \sigma^2 E^2$$

Accordingly, Eq. A(38) can be written:

$$P(k,R) = (\exp(ikR)/R)(\tfrac{1}{4}\pi) \int d^3 r \exp(ik \cdot r)[-(\sigma/2) \partial / \partial t \{\mu \in E^2 + B^2\} + B \cdot \nabla \sigma \times E - \mu \sigma^2 E^2] \qquad \text{A(45)}$$

where $\partial/\partial t$ remains, rather than being replaced by $i\Omega$. The reason for this is to emphasize that the $\Omega$ to use in k can vary from term to term. For instance, in the terms containing B, $\Omega$ depends on what comprises the magnetic field—i.e. whether B is to be the RF field or a static background field—or a combination of the two. For the $E^2$ terms, on the other hand, $\Omega$ is always twice the generating electromagnetic RF angular frequency.

To get some orders of magnitude, it is assumed that the RF field is a short pulse, so much so that in the direction of the observation point—i.e. along k—the amount by which a sound wave can move $\delta s$ is comparable with or shorter than an acoustic wavelength: specifically, assume that $k \cdot \delta s \ll 1$. This means that the wavelength of the ultrasound pulse is somewhat ill-defined, but the approximation of Eq. A(45) can provide insight. Secondly, assume that an acoustic lens is used to limit the area of the region perpendicular to k that is imaged onto the detector to $\delta A$. Then Eq. A(45) can be replaced by:

$$P(k,R) = (\tfrac{1}{4}\pi)(\exp(ik \cdot r)/R) \delta s \; \delta A [-(\sigma/2) \partial / \partial t \{\mu \in E^2 + B^2\} + B \cdot \nabla \sigma \times E - \mu \sigma^2 E^2] \qquad \text{A(45')}$$

Equation A(45') gives the pressure at the acoustic lens due to the $j \times B$ body forces in a small volume $\delta s \; \delta A$. The pressure at the detector can be increased from this pressure by the lens. Ignoring this increase for the moment, Eq. A(45') is used to estimate the magnitude of the pressure at the lens for the following values:

$$\delta s = 10^{-3} \text{ m}$$

$$\delta A = 10^{-6} \text{ m}^2$$

$$R = 10^{-1} \text{ m}$$

$$\sigma = 0.5 \text{ S/m}$$

$$\partial/\partial t \approx \Omega =\!> 10^7 \text{ sec}^{-1}$$

$$\nabla =\!> 1000 \text{ m}^{-1}$$

E=5000 V/m $B_{RF}=5\times10^{-3}$ tesla $B_0=0.1$ tesla $\varepsilon=80\times8.854\times10^{-12}$ F/m$=7.1\times10^{-10}$ F/m $\mu=4\pi\times10^{-7}$ H/m$=1.3\times10^{-6}$ H/m The values for δs and δA arise from the desired 1 mm resolution, (it is desired to be able to spot tumors as small as 1 mm on a side). The value for R is a representative distance from the surface of the body to an interior tumor. The value for σ is on the order of the conductivity of seawater, which is similar to the electrolyte conductivity values within a vascularized malignant tumor. The estimate for the frequency arises from the desire to use frequencies of a few MHz in order to get good electromagnetic penetration into the body and to have short enough pulse lengths to achieve resolutions along observation direction of the order of a millimeter. The estimate for the scale of variation of the conductivity comes from typical dimensions of different types of tissue in the body. This gradient can be larger in many instances. The estimate for E and $B_{RF}$ comes from the magnitude of the fields that are easily generated with coils external to the body. The electric field is also the order of magnitude that would be expected if applied by electrodes on the surface of the body. Finally, the magnitude of $B_0$ has been chosen so that the expense of the magnets or coils would not have to be as large as that for a typical MRI apparatus. It will be shown below that no static magnetic field is necessary for the charge density source, and that the resulting ultrasound signals are even larger than from the j×B source.

With these numbers, Eq. A(45') gives for the pressure at the acoustic lens from the small imaged volume:

With $B_0=0$ $P=10$ μPa

With $B_0=0.1$ tesla $P=0.2$ mPa

Thus, the largest contribution without a static B field arises from the B·∇σ×E term in Eq. A(45'). With these numbers, Eq. A(45') is approximated by:

$$P(\text{at lens})=>(\tfrac{1}{4}\pi)(\exp(ikR)/R)\delta s\ \delta A\ B\cdot\nabla\sigma\times E \qquad A(46)$$

For example, suppose the area of the lens is A, and that the area of the image formed on the transducer (of the same cross sectional area as the image) is δA, the same as the transverse area of the region being imaged. This does not allow for any demagnification that would reduce the image area and also does not allow for diffraction at the wavelength limit. By conservation of acoustic flux, it can be shown that:

$$P(\text{transducer})/P(\text{lens})=[A/\delta A]^{1/2} \qquad [A(47)]$$

As a numerical example, with no intent to be limiting, take $A=4$ cm$^2$ and $\delta A=0.01$ cm$^2$. Then, Eq. A(47) gives $P(\text{transducer})/P(\text{lens})=20$ i.e., keeping only the terms in Eq. A(46), $P(\text{transducer})=4$ mPa assuming a background field of 0.1 tesla in the same direction as the RF magnetic field.

Assume that a conventional PZT detector is used and is operated at resonance. Then, the voltage V generated on the detector can be estimated as:

$$V=g_{33}LQP(\text{transducer}) \qquad A(48)$$

where the simplifying assumption is implicitly made that the thickness of the transducer, $L<2\pi/k$. In this expression, $g_{33}$ is the piezoelectric voltage constant and Q is the quality factor of the resonance. Typical values are:

$g_{33}=25\times10^{-3}$ Vm/N(for PZT-4)

and, since the pulse length can be of the order of the RF period, we take $Q=1$. This gives $V=0.1$ μV.

For comparison, in the experiments reported below, the largest voltage recorded was 44 μV, as the input voltage to the amplifier. This indicates that the predominant mechanism for ultrasound production in this case was other than j×B.

In the foregoing, a conventional PZT transducer was assumed. No use has been made of any enhancement in signal that might be obtained by using the acoustic lens in a demagnification mode (which, incidentally, would have a negative effect on diffraction effects since demagnification would increase the linear dimension of the blur due to diffraction by the factor 1/demagnification). No use has been made of the larger signal that would be obtained from higher conductivity gradients that may occur within normal tissue and tissue in disease states.

Generation of Ultrasound from $\rho_q E$

The foregoing has also discussed the ultrasound pressure generated from the j×B=σE×B term in the ultrasound pressure wave equation (Eq. A(9)). Next consider the ultrasound pressure generated by the $\rho_q E=(\nabla\cdot D)E$ term in Eq. A(9), where $D=[\varepsilon+\sigma/i\omega]E\approx[(\sigma/i\omega)]E$ and where the approximate equality applies for the parameters of interest.

It is noted that unlike the j×B term, the $\rho_q E$ term contains a derivative of the conductivity. For an abrupt change in conductivity (as may be encountered, for example, in a malignant vascularization pattern), a way to estimate the ultrasound pressure resulting from the $\rho_q E$ source term is to use an approach based on the electromagnetic stress tensor $T_{ij}$, discussed earlier. This stems from the fact that the $\rho_q E$ term is largest where the gradient of the conductivity behaves like a delta function. This means that on either side of this region, Eq A(9) for the generated ultrasound pressure can be approximated by a source-free wave equation.

Accordingly, the $\rho_q E$ enters only as a boundary condition on the source-free wave equation. Specifically, at any point on the boundary $\delta P=n_i\delta T_{ij}n_j$ where $n_i$ denotes the ith component of the direction cosine of the surface normal, and δ indicates the change in the respective quantities. The treatment of a spherical source (section A1) is an example of this approach.

The terms of the stress tensor of Eq. A(13) that correspond to the $\rho_q E$ source term are $E_\alpha D_\beta-(\tfrac{1}{2})\delta_{\alpha\beta}E_\gamma D_\gamma.$ Specifically, they describe the effect of surface charges at interfaces. When the surface is perpendicular to E, these terms describe a tension per unit area normal to the surface:

$$T=-EAD/2 \qquad A(49)$$

On using Eqs. A(8) and A(10), this gives a tension of $$T = -\epsilon_0 \kappa E^2/2 => -(i\sigma/\omega)E^2/2 \quad \quad A(50)$$

The net tension on the surface is the difference between the tension on one side and the tension on the other:

$$\Delta T = -[(i\sigma/\omega)E^2/2]_1 + [(i\sigma/\omega)E^2/2]_2 \quad \quad A(51)$$

When the surface is parallel to E, the term describes a compression force of the same magnitude:

$$T = \epsilon_0 \kappa E^2/2 => (i\sigma/\omega)E^2/2 \quad \quad A(52)$$

and the net compressive force on the surface is the difference between the compressive forces on both sides:

$$\Delta T = [(i\sigma/\omega)E^2/2]_1 - [(i\sigma/\omega)E^2/2. \quad \quad A(53)$$

In one embodiment, suppose the surface between two regions of different conductivity is parallel to the electric fields. Then Eq. A(53) gives as the net stress per unit surface area:

$$\Delta T = (i\Delta\sigma/\omega)E^2/2 \quad \quad A(54)$$

Suppose:

$$\Delta\sigma = 1 \text{ siemens/meter} \quad \quad A(55)$$

$$\omega = 10^7 \text{ sec}^{-1} \quad \quad A(56)$$

For a direct comparison with the j×B —generated ultrasound pressure, the same electric field is used as before:

$$E = 50 \text{ volt/cm.} \quad \quad A(57)$$

With the same lens arrangement and the same PZT detector, the resulting transducer pressure and voltage at $\omega = 10^7 \text{ sec}^{-1}$ is:

$$P = 0.25 \text{ Pa} = 2.5 \text{ dynes/cm}^2$$

For Q=1 (for short pulse lengths) and g(33)=25×10⁻³ Vm/N gives

V=6.25 μV[detector voltage from $\rho_q E$ with no background magnetic field].

This result is a little larger than the voltage from a j×B source with a background magnetic field of 1000 gauss and can be compared to the 44 microvolt voltage that was found in the other experiments described below.

Note that the foregoing embodiment assumes the use of an acoustic lens with a magnification of 1 for the in vivo measurements, since the generated acoustic pressure in the body is assumed to be the same as that at the detector. An increase in detector voltage is always possible using a demagnifying lens if the detector dimensions are suitably scaled.

The simple order of magnitude results of this Section suggest that imaging in the human body with both the j×B and $\rho_q E$ generation of ultrasound is feasible with off-the-shelf transducers. For j×B, comparable signal intensity requires a large background static magnetic field of >1000 gauss. Images acquired without a background magnetic field will be weighted primarily from the $\rho_q E$ source of EM induced ultrasound. Image signal and contrast will depend specifically on the presence of a gradient in the conductivity.

A4. Signal Attenuation and Enhancement

Attenuation

Attenuation refers to the collective mechanisms for diminishing the ultrasound intensity as the pathlength through tissue is increased. Sample attenuation coefficients for 1 MHz ultrasound in various tissues are listed below in Table 2, (Matthew Hussey, *Basic Physics and Technology of Medical Diagnostic Ultrasound*. New York: Elsevier, 27 (1984)), along with the corresponding inverse absorption lengths for the ultrasound pressure (as opposed to ultrasound intensity).

TABLE 2

Attenuation of 1 MHz ultrasound

| Tissue | Attenuation coefficient for intensity $\mu$ (δB/cm) | Inverse attenuation Length for pressure $\alpha$ (cm$^{-1}$) [=0.115 $\mu$ (dB/cm)] |
|---|---|---|
| Water | 0.00002 | 2.3 × 10⁻⁶ |
| Fat | 0.6 | 0.07 |
| Brain | 0.6 | 0.07 |
| Liver | 0.7 | 0.08 |
| Kidney | 0.9 | 0.10 |
| Muscle | 1.0 | 0.115 |
| Heart | 1.1 | 0.13 |

The attenuation varies with frequency, increasing with frequency, f, in the range of 0.1–10 MHZ somewhere between $f^{1/2}$ and f.

In EMAI, the ultrasound signal is subject to attenuation resulting from a one-way trip from the region of interest to the detector rather than twice that pathlength as in conventional ultrasound imaging.

Acoustic Focusing

Ultrasound amplitudes can be magnified using acoustic lensing. Equation A(9) is a standard wave propagation equation with a source term; the same general considerations that define images in optical systems with lenses and mirrors can be applied here.

Figure 2:
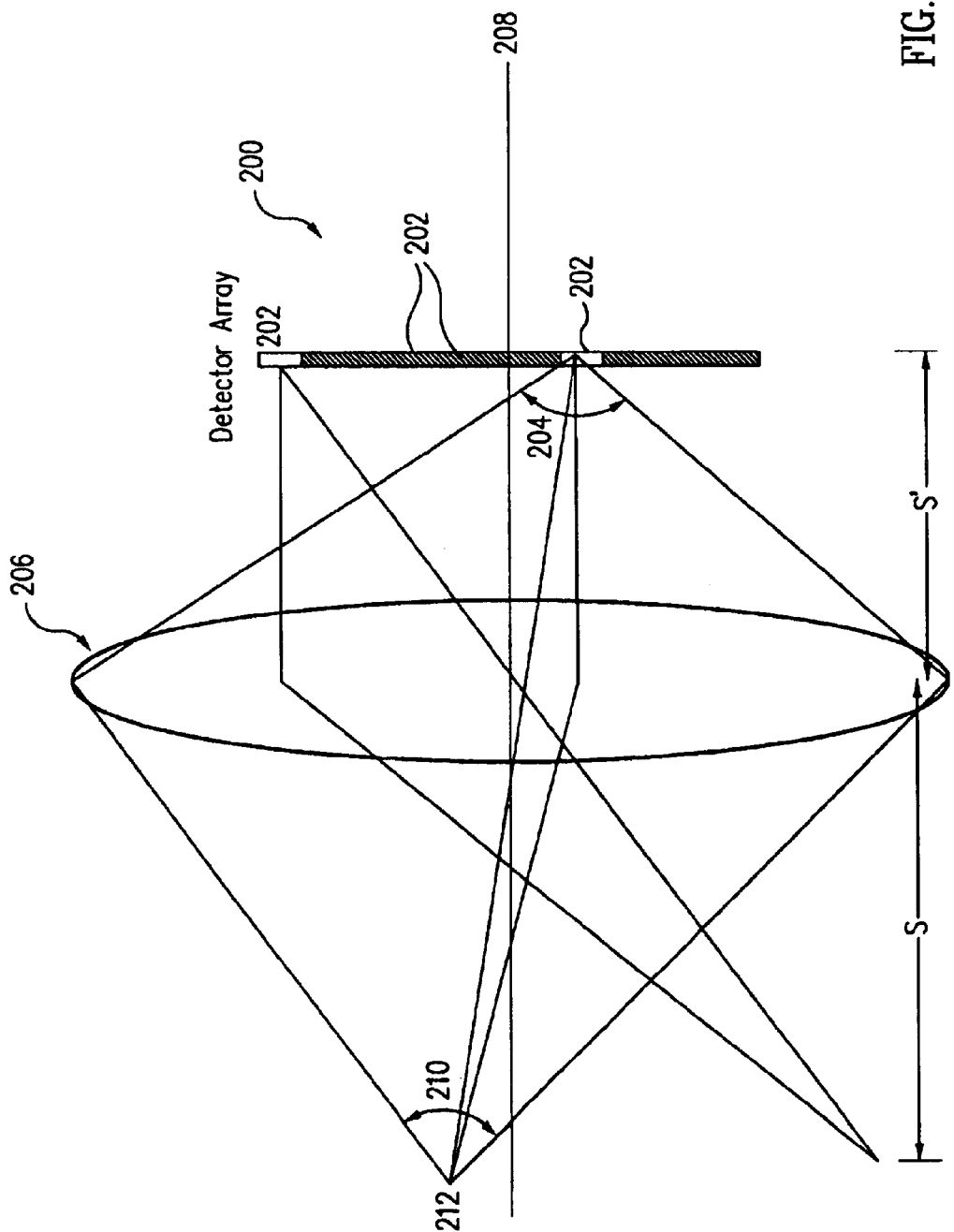
FIG. 2 is a simplified view of a slice through a large acoustic lens and an ultrasound detector array.

An acoustic lens or mirror can be used (with time-gating) to (1) limit the source volume viewed by a particular detector, and (2) increase the signal-to-noise at a detector. As illustrated in FIG. 2, when used with a detector array 200, the field of view for a particular detector element 202 is determined by the solid angle 204 subtended by lens 206 at its object point, where the distance s of the object point along the lens axis 208 is related to the distance s' along the lens axis of the corresponding detector element by the familiar lens equation:

$$1/s + 1/s' = 1/f$$

where f is the focal length of lens 206.

To limit the source volume to that in the vicinity of the object point, the signal at the detector element can be examined over the small time interval dt of the RF excitation pulse at the time that it takes an acoustic signal to travel from the object point to the detector element. Thus, the longitudinal resolution would then be given by $V_s dt$, where $V_s$ is the acoustic speed in the system. The transverse resolution would be determined by the conventional formulae of acoustic optics as detailed below.

The signal-to-noise at detector 200 is increased by the inverse of the lens transverse magnification, since it is the square of this factor that describes the ratio of the solid angle 204 subtended by lens 206 at detector element 202 to the solid angle 210 subtended by lens 206 at source region 212. For a large lens 206, this can be a large factor.

Acoustic Lens System Considerations

At least two imaging schemes are possible using acoustic lenses. In all cases it is preferable to have the interface between the volume of interest and the lens system planar.

This eliminates focal length changes and minimizes distortion due to velocity variations. In one embodiment, the focal plane within the interior could be selected through the use of a deformable, liquid filled plano-convex lens. The rigid flat side would be coupled to the skin or surface with a liquid or gel couplant and the flexible curved side would extend into a water tank containing the acoustic array. Focus would be adjusted by changing the curvature of the lens by adjusting the pressure of the enclosed fluid. The lens pressure would be sent to the ultrasound receiving/processing equipment, becoming a part of the record so that the focal length of the lens will be attached to the measurements. Note that in order for the plano-convex lens to converge an image, the velocity of propagation through the fluid within the lens must be slower than that of the fluid in the tank. The velocity of sound in the tank can be of the order of 1500 m/s. Examples of liquids having lower sound velocities are: acetone (1194 m/s), ethyl alcohol (1144 m/s), methyl alcohol (1103 m/s), benzene (1298 m/s), carbon disulfide (1149 m/s), carbon tetrachloride (924 m/s), chloroform (995 m/s). ether (985 m/s), heptane (1138 m/s)and octane (1171 m/s).

Figure 3:
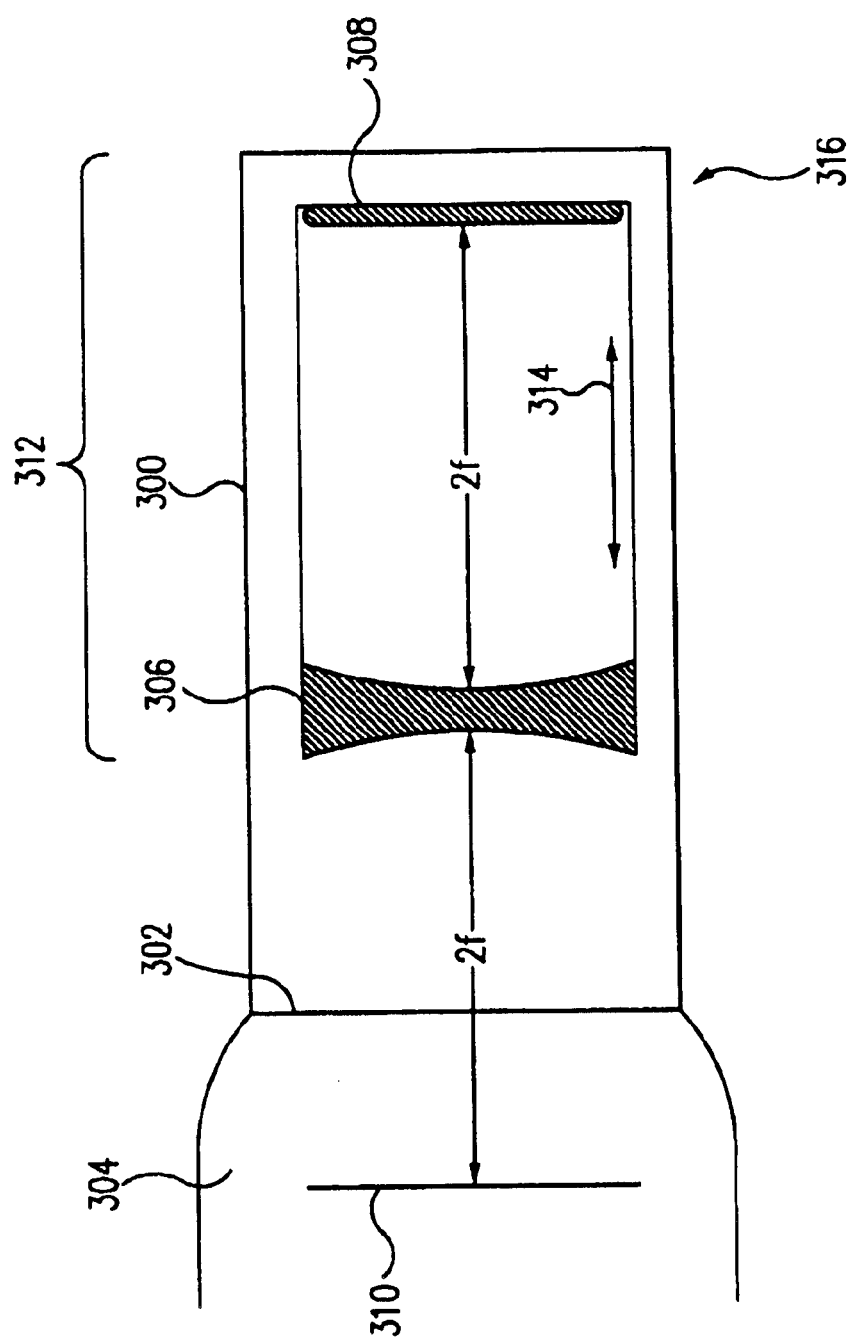
FIG. 3 is a simplified view of a lens and array assembly in a water tank adapted for breast imaging in accordance with an embodiment of the present invention.

In another embodiment illustrated in FIG. 3, a planar window 302 is used to interface water tank 300 to the volume of interest 304, using a liquid or gel couplant. Inside water tank 300 is a fixed focal length acoustic lens 306 and an acoustic array assembly 308. In one embodiment, if, for example, lens to array distance were fixed at twice the focal length of the lens, then object plane 310 would be at this same distance in front of lens 306 through planar window 302. The focus in the interior regions then would be selected by moving lens 306 and array 308 together as an assembly 312, in the direction indicated by arrow 314. When the sound velocity within those regions and in water tank 300 are approximately the same, the object distance is 2 f in front of lens 306. Because both the object plane 310 and image planes 316 remain fixed throughout the inspection process, this embodiment has the advantage of offering constant magnification (equal to one in this example). The magnification remains constant as the focus in the interior is changed, and planar interface 302 prevents distortion, simplifying image processing. In one embodiment, lens 306 can be made of a solid material, such as lucite. Lens 306 can have any shape depending on the actual sound velocity, such as plano-concave or double-concave lenses. Because the lens shape is fixed, it may be optimized for minimum aberration of the image. In this embodiment, the sound velocity is faster in the lens material than in the surrounding fluid. When using materials where the sound velocity is faster in the lens material than in the surrounding fluid, the shape of the lens is concave instead of convex.

Signal Averaging

The SNR may be further enhanced by signal averaging. As the signal accumulates in proportion to the number of acquisitions, N, and the noise in proportion to the square root of N, signal averaging can result in an increase in SNR proportional to $\sqrt{N}$. For short pulse lengths and high repetition rates, N can be high while maintaining total acquisition times within practical limits. Pulse repetition rates are constrained by the need to allow for dissipation of acoustic echoes, however numerical examples provided below demonstrate that desirable SNRs are obtainable.

A5. Image Parameters

The diagnostic utility of medical imaging generally depends on the degrees of spatial resolution and image contrast achievable and on the parameters giving rise to contrast. The diagnostic value of conductivity-weighted contrast has been discussed above and practical considerations for imaging such as acquisition time are presented below.

Resolution

The smallest practical transverse dimension resolvable is on the order of one wavelength of ultrasound. For typical sound velocity values in tissue this corresponds to a resolution of ~1.5 mm at a frequency of 1 MHz.

With an acoustic lens, the basic optics resolution limit is given by the diffraction angular limitation of $\lambda/D$, where $\lambda$ is the acoustic wavelength and D is the diameter of a typical acousto-optical element. An array of sensors can be used to increase D and improve the resolution. If the distance from the source to collection system is L, then the transverse resolution is roughly $(\lambda/D)L$.

To resolve the source along the lens axis, several possibilities exist: (1) a pulsed RF excitation source, (2) a chirped RF excitation source, and (3) Fourier transform tomography.

The induced surface charges at the interfaces between regions of different electrical conductivity exist only during the period when the RF excitation source is on. (This assumes fast charge relaxation times in the body, which is the case since plasma and collision times are of the order of $10^{-12}$ seconds.) Thus, an upper limit on the resolution distance b along the lens axis is determined by $$b = V_s t_p \quad \quad A(58)$$

where $V_S$ is the sound speed and $t_P$ is the pulse duration. Thus, with a sound velocity in the body of $1.5 \times 10^5$ cm/sec, to get a (longitudinal) resolution of 1 mm, pulse lengths can be in the order of 1 microsecond. If the pulse is furnished by a transient current in a coil adjacent to the body, the pulse power required can be estimated by regarding the body as a shorted secondary (with a finite impedance) in a transformer in which the primary is the coil. Accordingly, the type of electric fields desired can be obtained from readily commercially available power sources. Specific power requirements are discussed further below.

In another embodiment, good resolution along the lens axis is obtained by chirping the RF source (i.e. to vary the frequency of the source with time). Since the equations of Section A1 show that the ultrasound generated is at twice the RF excitation frequency, the location of the ultrasound source can be correlated with the detected frequency of the ultrasound. If the bandwidth for receiving the ultrasound is $\delta f$, and the sweep rate for the source chirp is $df/dt$, then the longitudinal resolution is of the order of:

$$b = V_s \delta f (df/dt)^{-1} \quad \quad A(59)$$

In practice, the duration of the chirped pulse could be chosen so that the product of the speed of sound and this duration would equal the longitudinal linear dimension of the total region to be imaged.

Fourier transform tomography also can be used to obtain information on the spatial distribution of the conductivity gradient in the body. From Eq. A(9) with only the $\rho_q E$ source term present and conductivity dominating the effective dielectric constant, it can be shown that:

$$\nabla^2 P - V_S^{-2} \partial^2 P/\partial t^2 => \nabla \cdot [(\sigma/i\omega)E]E \quad \quad A(60)$$

Then, at the ultrasound wave number, k, corresponding to an ultrasound angular frequency $\Omega$:

$$P = (1/4\pi R) \int dV \exp(ik \cdot r) \nabla \cdot [(\sigma/i\omega)E]E. \quad \quad A(61)$$

Equation A(54) shows that when the gradient of the conductivity is much larger than the gradient of the electric field, the pressure is a (weighted) Fourier transform of the gradient of the conductivity. Thus, different orientations of the lens give different (weighted) Fourier transforms of the gradient of the conductivity.

Contrast

Contrast provided should be large relative to that obtainable with ultrasound imaging alone because of the large ratio of conductivity values in the body versus the small acoustic reflection coefficients. As described in Section A2, variations in conductivity values are on the order of several hundred percent. When these variations occur over short dimensions, as across vascular endothelium for example, the conductivity gradient is increased with a beneficial effect on image contrast.

A6. Generalization from Conductivity Imaging

In the foregoing, the emphasis has been on imaging the conductivity gradients in the body. For tissue, however, it is well known that the electrical response has both real and imaginary parts, with the magnitude of each dependent on frequency. Thus, a Cole-Cole plot for a tissue admittance (i.e. plot of the real and imaginary loci of the tissue's electrical admittance with frequency as a parameter) typically displays an arc that resembles a (distorted) semicircle with a center below the real axis. At the higher frequencies, the real part (i.e. the conductive part) is dominant.

It is worthwhile pointing out that as the frequency is lowered, the susceptance parts of the admittance response can also contribute to the image. As a simplified example, consider the admittance of a simple cell, one of millions comprising the tissue. As an approximation, attribute the conductive portion of the admittance to the electrolyte and the susceptance portion to the capacitance of the cell membrane encapsulating the cell. The magnitude of the electrolyte conductance is thus of order of $\sigma L$, where L is a characteristic linear dimension of the cell, and $\sigma$ is the electrolyte conductivity, and the magnitude of the susceptance of a cell membrane is of the order of $\omega \in L^2/d$, where $\in$ is the electrical permittivity of the membrane material, and d is the membrane thickness.

Then, since the electrical path through the cell consists of two membranes in series with the interior electrolyte, the reciprocal of the total cell admittance is equal to the sum of the reciprocals of the electrolyte conductance and twice the reciprocal of a membrane susceptance. Thus, the ratio of the susceptance portion to the conductance portion of the cell admittance is of the order of:

Cell susceptance/Cell conductance=$O[2\sigma d/(\omega \in L)]$ where the factor of 2 arises from the presence of two membranes in the traversed path through the cell.

For a 100 micron cell with an 80 Angstrom thick membrane, $\sigma=1$ Siemen/meter, and a membrane relative dielectric constant of 5, Cell susceptance/Cell conductance=$O[2.8\times10^{-7}s\omega]$.

Thus, at $\omega=10^7$ sec$^{-1}$, the cell susceptance can be comparable with that of the cell conductance. This is qualitatively consistent with the tissue admittances of Table 1, although the experimental numbers there show the susceptance can be less than 0.1 of the conductance. The addition of extracellular electrolytes can contribute to the lower experimental ratios. Accordingly, by examining both the in-phase and 90-degrees out-of-phase portions of the ultrasound pressure generated, both the conductance and susceptance portions of the body can be examined. (Note that in general the conductance and susceptance contribute differently to the in-phase and 90-degrees out of phase portions.) Phase may be determined relative to that of the time reference signal delayed by half the round trip transit time an acoustic signal emitted by the transducer and reflected by the gradient or discontinuity imaged.

A7. Power Requirements

In one embodiment of the RF pulse excitation system, a charged capacitor is provided being discharged through a resistor into a coil. To image the breast, for instance, the coil could surround the breast. To begin the discharge, an electronically activated rapidly closing switch, such as a spark gap switch, hydrogen thyratron, or a bank of silicon controlled rectifiers can be used to cause the charged capacitor to discharge through a resistor in series with the coil inductor. This arrangement forms a tuned RLC circuit that rings down at a frequency determined by the values of the capacitor and inductor. The value of the resistor can be chosen so as to create a damping time comparable to the desired pulse length. This can create a damped oscillatory RF burst lasting on the order of a microsecond, inducing an electric field in the breast that can generate the desired ultrasound. After the discharge, the capacitor can be recharged by opening the same electronically activated switch used earlier to complete the RLC resonant circuit. Note that a possibly slower opening time of the switch does not present a problem, since the pulse duration is determined by the Q of the primary circuit and not by the opening of the switch. During the subsequent charging phase, the capacitor can be charged by a current source, with the charging occurring over a much longer period—of the order of a millisecond. The discharge and charging process can then be repeated for as long as necessary to complete the breast inspection.

To estimate power source requirements, a straightforward circuit analysis can been done on the foregoing topology, treating the breast as the resistive secondary of a resonant transformer in which the primary consists of the induction coil, the charged capacitor, and the damping resistor. In this embodiment, with a resonant angular frequency of $10^7$ sec$^{-1}$, the instantaneous power dissipation is larger in the primary circuit than in the breast itself, and the peak envelope power (PEP) during discharge is of the order of 10's of kilowatts. On the order of 90% of the power is dissipated in the tuned circuit and on the order of 10% is dissipated in the breast. The corresponding capacitive voltages are somewhat less than 10 kilovolts, and the primary circuit currents are tens to hundreds of amps. The actual values depend on the L/C ratio and the actual power required.

It is of interest to observe how the power dissipation varies with the desired fields and parameters. The circuit analysis leads to the following scaling laws for the peak envelope power dissipated in the primary circuit resistance during the discharge:

$P(\text{watts})=1.4f(\text{Mhz})D^3(\text{inches}^3)B^2(\text{gauss}^2)/Q$ and $P(\text{watts})=888D(\text{inches})E^2(\text{volts}^2/\text{cm}^2)/[Qf(\text{Mhz})]$ In these expressions, f is the resonance frequency, D is the diameter of the induction coil, B is the axial field created by the coil, Q is the ratio of the reactance to the resistance in the primary discharge circuit, and E is the azimuthal field created by the coil near the coil radius.

This description of a charging/discharging system is by no means meant to exclude other possible RF excitation systems, for example, RF burst generator and amplifier chain. Many alternative RF excitation systems, commercially available or custom made, can be used.

A8. Introduction of Electric Fields into the Interior of a Conducting Body

In one embodiment, the present invention introduces time-varying electric fields into the conducting medium that in turn generate the imaging ultrasound waves. The introduction of the electric fields is done in such a way as to avoid inducing charges on the surface of the conducting medium that would shield the interior from the electric fields. This can be done in several ways. Two practical means are (1) to introduce time-varying magnetic fields into the medium, and (2) to introduce currents into the medium with ohmic contacts at the surface.

The use of time varying magnetic fields has the advantage that no direct contact of the conducting medium with the external power source is required. Instead, the magnetic fields can be introduced into the medium as a result of currents flowing in external conductors. The time-varying magnetic fields in the medium then create by induction associated electric fields in the medium. In a medium with complicated geometry, the associated electric fields can best be visualized by application of Lenz's law, aligning the electric fields with current flow lines, and constraining the current flow lines by the surfaces of the medium.

The use of direct current injection into the medium via electrodes is familiar from electrical stimulation therapies and from ohmic tomography. The electric fields are aligned with the current via Ohm's law. At the frequencies of interest (where the free-space wavelength is much larger than the conducting medium dimensions), the distribution of the field lines can in principle be obtained by solution of Laplace's equation in the medium, taking the field lines to be tangential to the medium surfaces at all points except where the currents are injected and recovered.

Capacitive coupling can also be used to introduce the fields into the conducting medium as long as the capacitive gaps at the surface are small in order to avoid most of the voltage being dropped across the gaps themselves.

A9. Safety Limits for Medical Applications in Humans

EMAI uses radiation with RF electromagnetic fields as is currently performed for MRI. FDA guidelines specify a limit on the amount of power that may be deposited in human tissues: Not more than 8 W/kg may be deposited in any gram of tissue in the head or torso and not more than 12 W/kg may be deposited in a gram of tissue in the extremities for any period of five minutes U.S. Department of Health and Human Services, Food and Drug Administration, Center for Devices and Radiological Health, "Guidance for the submission of pre-market notifications for magnetic resonance diagnostic devices", US DHHS FDA, Rockville, Md., 1998; International Electrotechnical Commission, "Medical electrical equipment-Part 2: Particular requirements for the safety of magnetic resonance equipment for medical diagnosis," International Standard 60601-2-33 International Electrotechnical Commission, Geneva, 1995.

In this imaging method, power deposition is related to the mechanical pressure arising from the electrical stress, of order:

$$T(R,\theta) \sim (\in + \sigma/\omega i) \times E^2(R,\theta)/2 - P(R,\theta)/\omega i \qquad A(62)$$

since $\in \ll \sigma/\omega$ in soft body tissues. Here $P(R,\theta)$ is the power dissipated per unit volume at the source surface given by the radial coordinates $R,\theta$; $\in$ is the dielectric constant, and $\sigma$ is the conductivity.

The FDA limit above gives:

$$P(R,\theta) \leq P_{Max} = 8 \text{ watts/kg} \sim 8 \text{ kW/m}^3 = 8 \text{ mW/cm}^3. \qquad A(63)$$

The guidelines specify that these power densities must apply down to one gram of tissue, i.e. ~one cubic centimeter. Thus for smaller volumes the power density limit may be exceeded provided that, when averaged over a cubic centimeter, the limit is met.

By Eq. A(62), both the desired signal strength and the power deposition are proportional to the square of the electric field, the tissue conductivity, and inversely to the RF frequency. Thus, while higher field strengths serve to increase SNR, safety standards constrain the E field and/or duty cycle (fraction of time the RF pulse is on) that may be used for given endogenous conductivity gradients.

For a numerical example with no intent to be limiting, consider an RF pulse of 0.5 MHz with an electric field of E=V/cm and a region of interest that can be characterized by a conductivity of 0.33 S/m. Then a resistive power of $jE/\rho = \sigma E^2/\rho = 8250$ watts/kg is deposited within the region. Here $\rho$ is the mass density. A 0.094% duty cycle satisfies the FDA requirements of 8 W/kg and can be achieved by 1 microsecond long RF pulses repeated about every millisecond, i.e. 1000 pulses per second. This repetition rate also allows for reflections from the surface of the body to die down between pulses. Next, consider a detector located 15 cm away from a source of induced ultrasound. The pressure generated depends on the convergence of the electric field lines which in turn depends on the scale over which the region of interest may be characterized by a given conductivity. It can be shown that for a 1 mm region, this convergence causes the electromagnetic pressure to increase by a factor of 4.5 over the far field pressure, $\in E^2/2$. For a convergence factor, CF, of 4.5 and power deposition of 8250 watts/kg, the pressure generated during a 1 microsecond RF pulse is $$P(\text{source}) = O[0.33 \times (4900)^2/2\pi \times 0.5 \times 10^6]CF = 11 \text{ Pa}.$$

In the presence of regions one centimeter or more in radius field convergence necessitates reducing the applied field strength by a factor of 4.5, while for 1 mm radius the convergence is confined to a volume much less than one cc so the field need be reduced by only 1.3%, thus the reduction of E from 5000 V/m to 4900 V/m in the equation above. Then the pressure at the detector location is of the order of:

$$P = O[11 \times (0.1/15) = 0.073 \text{ Pa}].$$

For a typical PZT crystal detector, this gives a detector signal of 1.9 microvolts across 50 ohms. For a bandwidth of 7 MHz, the noise power of the 50 ohm resistor at 290° K=62° F. is 28 fW, corresponding to a noise voltage of 1.2 microvolts. Thus, the ratio of the signal voltage to the noise voltage is:

$$SNR = 1.9/1.2 = 1.6$$

To get the signal/noise up to 100, the signal from $(1.6/100)^{-2} = 3906$ pulses would have to be averaged. At 1000 pulses/sec, this would take about 4 seconds. Alternatively, if lens 306 described above (FIG. 3) were to be used, the pressure at detector 308 would be larger than 0.073 Pa by a factor of 20, (i.e. the pressure at the detector would be 1.5 Pa). This would give a transducer voltage of 38 microvolts and a SNR of 32 without signal averaging across 50 ohms. Averaging the ultrasound from only ten pulses would produce a SNR of 100.

A10. Frequency Intermodulation

With single frequency electromagnetic excitation, EMAI generates an acoustic signal at twice frequency (2 f). The ultrasound results from the vector product of the applied magnetic field acting on tissue containing a charge, which in turn results from the induced electric field acting on the conductivity gradient. Because both the magnetic field and the charge are bipolar AC signals of the same frequency, their product produces a twice frequency and a DC component. One way to visualize generation of the twice frequency signal is to consider the sign of the product of two same frequency sine waves. When both waves are positive, the product is positive. But when both waves are negative, the product is also positive. Thus the product contains two complete cycles for each incident cycle, generating the twice frequency component.

The foregoing process can be considered nonlinear in the sense that the two signal components are multiplied together as opposed to linear addition. In many respects, the phenomenon is analogous to a nonlinear circuit element such as a mixer, a full wave rectifier, or an absolute value circuit. In one embodiment, in excitation with two frequencies, the dominant signals present after the nonlinear process are the two fundamentals (f1 and f2), their frequency doubled components (2 f1 and 2 f2), their sum and difference frequencies (f1+f2 and f1−f2), and twice these frequencies (2 f1+2 f2 and 2 f1−2 f2). Of particular interest are the sum and difference components.

The ability to receive on a frequency different from the high power transmitted signal (or a harmonic thereof) allows faster receiver recovery time in a pulsed system and continuous, interference-free reception in a CW system. This can result in enhanced sensitivity and a reduced "blind zone" or minimum detection distance.

By employing two driving EM frequencies, and tuning the sensing devices to either the sum or difference frequency, avoiding the fundamental or harmonic of either driving signal, the signal-to-noise in the sensing transducer and circuitry is improved, which improves signal quality and reduces overall cost.

The following experiments are meant to provide experimental proof of principle, but are in no way intended to limit the invention.

B1. Experiment 1

Figure 4A:
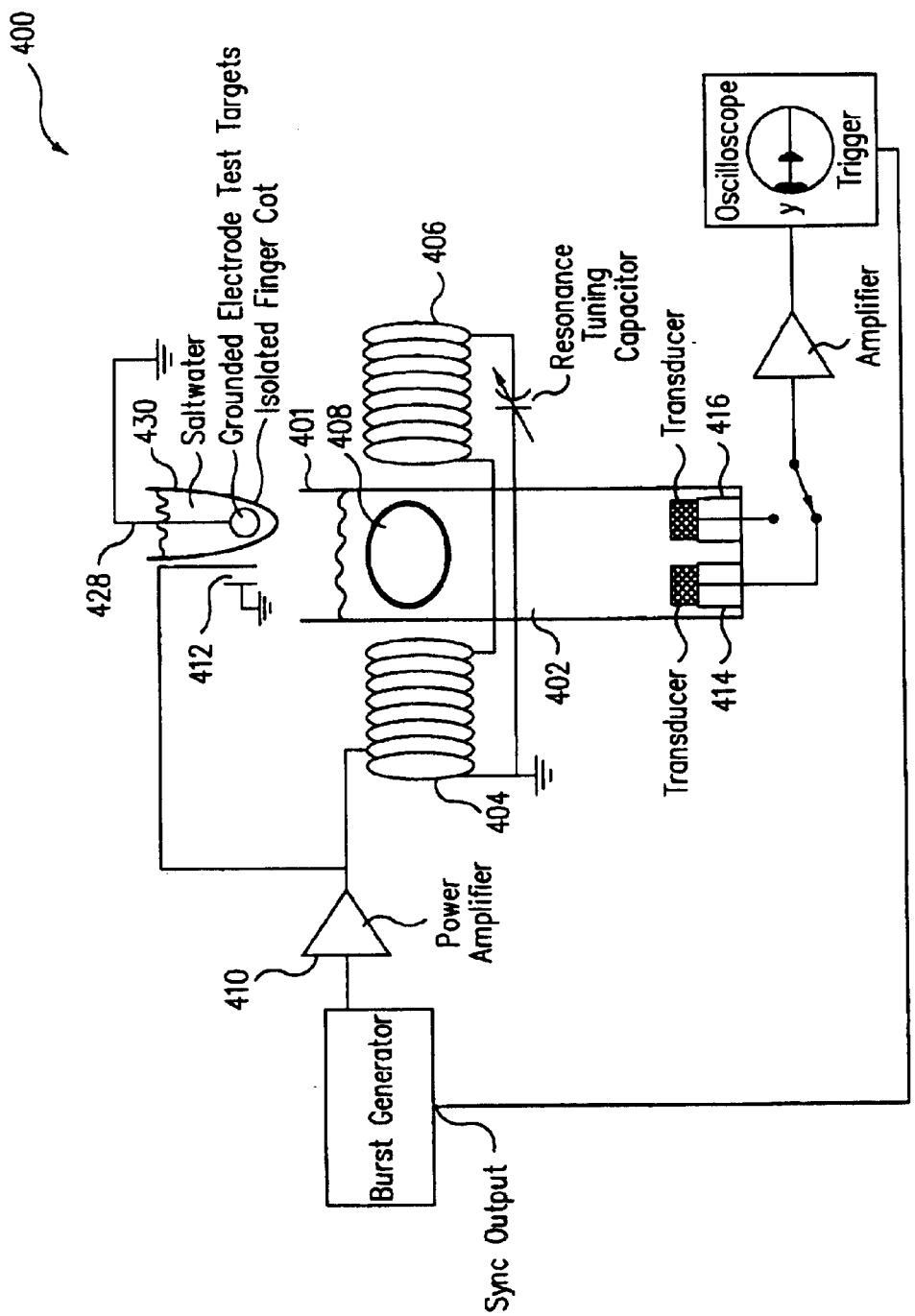
FIG. 4A is a simplified diagram of the vertical water column and split horizontal solenoid producing ultrasound from electrical stress on a conducting surface with Ultrasonic sensors at the bottom of the vertical column.

FIG. 4A is a schematic drawing of an experimental apparatus 400, used to demonstrate that ultrasound can be generated by surface charges at an interface between conducting and non-conducting media. FIG. 4A shows a vertical cylinder 401 holding a liquid 402, such as saltwater and a pair of horizontal solenoids 404 and 406 yoked together, providing a magnetic induction field in immersion volume 408. An RF power amplifier 410 feeds solenoids 404 and 406. A capacitor probe 412, which can be inserted in cylinder 401, includes two conducting plates separated by a thin gap. Two piezoelectric sensors 414 and 416 are located at the bottom of cylinder 401. A pulsed RF current source is used to excite the conducting plates of the capacitor probe 412 and/or solenoids 404 and 406.

In Experiment 1, the excitation frequency is 2.25 MHz, and the duration of the pulse is 10 microseconds. The resonant response of piezoelectric (PZT) sensors 414 and 416 is at 2.25 MHz, and 5.0 MHz, respectively. The RF transmitter source has selectable power outputs at 4, 16, 300, or 350 watt, feeding into 50-ohm impedance. A peak voltage of 2.6 kV is impressed on the solenoid, and when the capacitor probe is used, one side of the probe is at ground.

The frequency of the excitation was adjusted to give maximum output from the transducer in use. Up to 1 kG of field from a permanent magnet did not appear to affect the results.

A grounded electrode 428 was placed inside a finger cot 430 with salt water contained within and outside the insulating wall of cot 430. Electric fields are produced by magnetic induction through a current loop, which included the capacitor formed by the insulation of finger cot 430 and grounded salt water on both sides. Ultrasound signals (76 microvolts at the transducer before amplification) are received at the excitation frequency of 2.25 MHz and at 4.5 MHz with a time delay (145 microseconds) corresponding to sound propagation between finger cot 430 and PZT sensors 414 and 416. When the conductor in finger cot 430 included the two conducting plates of capacitor probe 412, the signal was independent of the orientation of the plates with respect to the solenoid axis, and indeed the signals were present even when the electric field was provided by direct electrical connection and solenoids 404 and 406 were not activated. Analysis of the results using the approach of Section A indicated that the sources of the signals were surface charges electrically induced on finger cot 430 interface between the salt water inside and outside.

To summarize, in the experiments conducted with the apparatus of FIG. 4A, electric fields acting on surface charges produced measurable ultrasound consistent with the calculations presented in Section A.

B2. Experiment 2

In Experiment 1, ultrasound generation was demonstrated from surface charges induced on an interface between a conducting region and a non-conducting region. Experiment 2 demonstrates ultrasound generation at an interface between two regions of different conductivity. In Experiment 2, ultrasound generation is demonstrated from surface charges induced on an interface between two regions of different conductivity.

Figure 4B:
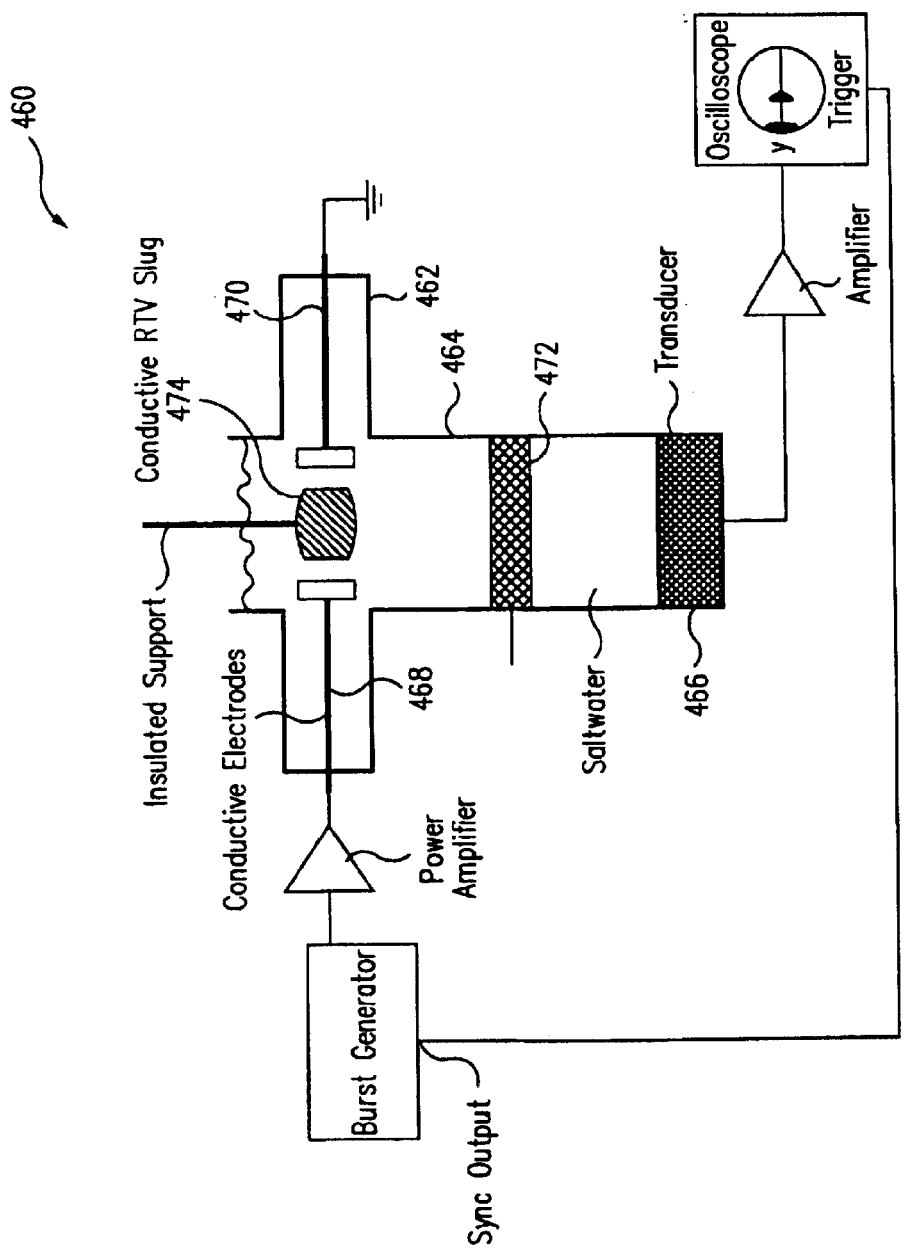
FIG. 4B is a simplified diagram of an apparatus, used for ultrasound production at an isolated interface between two regions of different conductivity.

The apparatus 460 of Experiment 2 is shown in FIG. 4B, which includes two intersecting PVC ½ inch pipes, one horizontal 462 and the other vertical 464. A 5 MHz PZT detector 466 was placed at the bottom of vertical pipe 464, about 6 inches below horizontal pipe 462. Two electrodes 468 and 470 were placed in the horizontal pipe to provide horizontal current. A ring electrode 472 was placed in vertical pipe 464 as well, below the intersection with horizontal pipe 462. In Experiment 2, ring electrode 472 was disconnected when the pair of electrodes 468 and 470 facing each other were oppositely charged; alternatively, these two electrodes were electrically connected and opposite polarity was applied to ring electrode 472 producing vertical current flow in the salt water.

In one series of experiments, a cylinder (0.36" diameter× 0.5" long) of Moreau MMS-020-1 Nickel Graphite conductive RTV silicone rubber 474 was placed in the intersection of the vertical and horizontal pipes. The axis of the target was vertical, and it was suspended in the intersection by an insulated support. The horizontally spaced electrodes were used. These were 0.45" in diameter and spaced 0.7" apart. The electrolyte in the arms was saltwater, approximately 80:1, water:salt by volume. The distance between the RTV target and the top of the PZT sensor was 4.25". A 2.2KW peak envelope power, 380 volts peak to peak, RF pulse at 2.5 MHz and 10 microsecond duration was used to drive a horizontal current through the target. An ultrasound signal was observed at the PZT detector at twice the excitation frequency. The transducer voltage was 40 microvolts peak to peak before amplification to 40 mV. The time delay corresponded to the one-way travel time for an acoustic pulse from the target to the transducer.

The experiment was repeated with vertical current and virtually the same results were obtained (a 50 microvolt signal).

The resistivity of the RTV target was nominally 0.01 ohm cm, much less than the resistivity of the surrounding salt water. The experiment was consistent with the hypothesis that surface charge induced on the interface between two regions of different conductivity generates an ultrasound pulse at twice the electric field excitation frequency.

Thus, in a 1 dimensional approximation, the outward propagating pressure from a region of dimension 2a and conductivity σ(inside), is $$P(x)=[\Delta\{(E^2)(\sigma/i\omega)\}] \exp[-ik(\text{outside})(x-a)](1/G)$$

where x>a is the distance at which the pressure is evaluated, k(outside) is the wave number in the region external to the inner region for 2ω, ω is the angular frequency of the RF excitation electric field E, and Δ designates the difference of the values inside and outside. The factor G is a geometrical factor that depends on the ratio of the wavelength inside to the dimension of the region:

$$G=1+i[k(\text{inside})\rho(\text{outside})/k(\text{outside})\rho(\text{inside})] \cot[k(\text{outside})a]$$

where k(inside) is the wave number inside the region for a wave of angular frequency 2 ω, and ρ designates the density.

When E is perpendicular to the surface of the inner region (which will be the case if the inner conductivity is much bigger than the outer conductivity, as is the case in the RTV experiment), then the Δ{ } in the expression can be replaced approximately by the value of the expression outside the region, since E(inside) is so much smaller than E(outside).

Since Abs(G)>1, the maximum possible value of P is $\{(E^2)(\sigma/i\omega)\}$(outside). For the horizontal electrodes, Voltage=380 volts Distance between electrodes=0.7 inches so that $E$=21372 V/m Then, since Poisson demonstrated that isotropic materials have a Poisson ratio of 0.25, this gives $P$(max) in vertical column=3.6 N/m²

Then, with $g$(33)=25×10⁻³ Vm/N

PZT thickness=1 mm=10⁻³ meter.

The maximum PZT voltage would be:

$V$(horizontal)=$g$(33)(PZT thickness)(Pressure(max))=90 microvolts.

The measured voltage was 40 microvolts with the horizontal electrodes.

For the vertical electrode excitation, the Poisson ratio would not be totally present as a factor, but the electric field would be smaller since the electrode spacing was much larger than 0.7 inches. With an electrode spacing of 1.5 inches, the voltage would be $V$(vertical)=90 microvolts×(1/0.25)×(0.7/1.5)²=78 microvolts.

The measured voltage was 50 microvolts with the vertical electrodes.

The experimental values are consistent with those estimated from the electric stress tensor. Several factors contribute to the difference between the value expected and the measured value. The geometrical factor G would reduce the predicted values from those indicated and discrepancies may also be explained by 1) the fact that the acoustic wavelength is much less than the size of the cylinder which means that the estimate is an upper limit to the sensor pressure expected and 2) the 1D approximation gives an upper limit since it assumes phase coherence instead of the opposite extreme of random phase.

Note that the conductivity and field parameters used in the demonstration experiments are different from the parameters described earlier for physiological applications. The experimental parameters were designed such that signal averaging and acoustic lensing would not be required to demonstrate that the proposed electromagnetic generation of ultrasound operates as expected. The analyses of Section A (especially Section A6) show that with signal averaging and acoustic lensing, the same mechanism can be used for imaging in the human body with acceptable fields and acceptable signal averaging times.

Embodiments with numerical examples are proposed for medical diagnostic imaging applications for EMAI. EMAI may be used alone or in combination with conventional ultrasound. The embodiments presented here range from inexpensive and easily constructed configurations to relatively more costly devices. The suggested devices may be applied to a variety of medical applications.

C1. Acoustic Lenses and Detector Arrays

In this example embodiment, an array of ultrasonic sensors is used in conjunction with an acoustic lens (FIG. 2). This configuration allows for desired image resolution within practical acquisition times.

Denoting the focal length of the lens by f and the distance from the lens to the array by s', familiar ray optics shows that the distance s to the region being imaged is given by:

$$1/s+1/s'=1/f \qquad C(1)$$

Also shown in the figure is the particular voxel that is imaged by a particular array element as determined by conventional ray optics. The longitudinal resolution along a ray is determined by the length of the excitation pulse dt and the time that it takes for the acoustic signal to travel from the voxel to the array element. Denoting the distance from the lens axis of the particular array element of interest by R, the distance r from the lens axis of the imaged voxel is given by $$r/s=R/s' \qquad C(2)$$

and the time t required for the acoustic signal to travel from that voxel to the array element is $$t=\sqrt{[r^2+s^2]^{1/2}+[R^2+s'^2]^{1/2}}/V_S \qquad C(3)$$

Thus, if the signal at that particular array element is sampled for a pulse duration dt at a time t after the excitation pulse, a resolution along the ray of the O($V_S$ dt) isl obtained, where $V_S$ is the acoustic velocity. For instance, if $V_S$=1.44×10⁵ cm/sec, and dt=1 microsecond, the resolution along the ray is 1.44 mm. The transverse resolution can be set to the same amount by choice of the lens and array parameters. For instance, the transverse angular resolution is determined by the ratio λ/D where λ is the acoustic wavelength and D is diameter of the acousto-optical element (and that the dimension of the array detector elements is of the order of a wavelength in order to avoid phase cancellation on a detector element). Then for a lens magnification of unity and a focal length of 10 cm, say, the transverse resolution would be of order of (0.1/10)×10=0.1 cm. Thus both the transverse and longitudinal resolutions would be on the order of 1 mm. Aberrations may occur and the array element spacing and surface and the imaging surfaces may be adjusted to compensate.

Suppose for example that a 100×100 array of 1 mm×1 mm elements is used. This can be obtained inexpensively by dicing a large PZT wafer with a slitting and feeding the output of the array into a very large scale integration ASIC (Application Specific Integrated Circuit) that digitizes at 1 GHz and scans by row or column.

Next, suppose it is desired to scan a 10 cm×10 cm×10 cm volume with voxel resolution of 1 cubic millimeter. Then either f or s' will need to be changed 100 times during the scanning. This can be done for example by changing the pressure in a fluid filled lens, or by mounting the lens/array or array itself on a motor-driven stage.

If the lens results in an increase in the ultrasound signal at the detector by a factor of 100 (since it overcomes the 1/R decrease in acoustic signal where R is the distance from the source to the detector), then the data gathering time for a particular voxel can be reduced by $10^4$ to obtain a given S/N. But since 100 different f or s' would be needed to scan the volume, the net gain would be of order $10^4/100=100$, i.e. a reduction in the imaging time by the order of 100 is possible.

Using a signal to noise ratio of 32 as calculated in section A9, the signal averaging time for a given voxel for typical physiological parameters is of the order of 10 milliseconds. Assuming parallel electronic processing, this becomes the time required for each of 100 slices of the million voxel image. Thus the whole image could be acquired in the length of time for one hundred focal adjustments. In one embodiment, these adjustments may be done continuously over a period of several minutes. Since only ten milliseconds would be required to image each slice, there would be negligible blurring during this slow adjustment.

Because the number of voxels that can be imaged with this approach is $(L/dx)^3$ where L is the total linear dimension scanned and dx is the minimum voxel resolution, dimensions for L and dx of 10 cm and 1 mm, respectively, will allow for distinguishing up to $10^6$ separate sources.

To change the particular depth (i.e. axial distance from the lens) of voxels that are imaged by the acoustic lens onto an array element, we have discussed changing the position of the lens and/or the position of the array to satisfy the simple lens equation that relates focal length, object position, and image position. Another interesting possibility that does not require any component translation is to use an acoustic lens that consists of an encapsulated fluid in which sound speed is different than that of the medium to be imaged. The focal length of such a lens can be changed simply by changing the amount of fluid in the lens. This in turn can be accomplished by changing the pressure in a connected fluid reservoir. For a fixed distance between the lens and the array, the effect of the change of focal length is to image voxels at different depths onto the array. Note that the magnification also changes with this approach which can be compensated for with computer processing.

C2. Holography (Fourier Optics)

The use of a large array without a focusing lens also permits data processing with familiar Fourier-optics algorithms. In particular, imaging with electromagnetically induced ultrasound lends itself to holographic reconstruction of the spatial variation of conductivity gradients as Eq. A(38) may be recognized as its Fourier transform.

This approach uses a relatively large array of transducers to simultaneously receive the acoustic energy over an appreciable aperture. For example, the array could take the form of a circular (or square) disk 2" to 3" in diameter directly coupled to the front of the breast with a coupling gel. The phase and amplitude data across the array is processed using a holographic algorithm to generate a 3 dimensional acoustic image of the signal sources in the breast (in this respect it is an expansion of a simpler 3 transducer method described below). It offers significant advantages in imaging quality, especially if multiple, diffuse, or extended sources are involved.

C3. Simple Sensor Array

An embodiment incorporating a limited number of detectors can be applied to situations in which a few well-separated sources are present. In this relatively inexpensive approach, the transit time of the ultrasonic signal resulting from an RF burst irradiating a compressible region containing a conduction gradient or discontinuity is used to determine its distance, $L_A$, $L_B$, $L_C$, from each (at least three) of a small number of detectors. With three detectors at corners A,B,C of an equilateral triangle [at Cartesian coordinates $A=(-D,0,0)$; $B=(D,0,0)$; $C=(0,\sqrt{3}D,0)$ below the volume of interest, the coordinates of the RF-induced ultrasound source are given by:

$$x=(L_A^2-L_B^2)/4D \qquad C(4)$$

$$y=\{(L_A^2+L_B^2)/2-L_C^2-D^2\}/2\sqrt{3}D+D\sqrt{3}/2 \qquad C(5)$$

$$z=\sqrt{L_B^2-y^2-(x-D)^2} \qquad C(6)$$

with D equal to half a side of the sensor triangle. If there is more than one source, associating measured transit times, $\tau_A$, $\tau_B$, $\tau_C=(L_A, L_B, L_C)/V_s$ with a single source can be checked by re-computing $L_A$, $L_B$, $L_C$ from:

$$L_A=\sqrt{[(D+x)^2+y^2+z^2]} \; L_B=\sqrt{[(D-x)^2+y^2+z^2]} \; L_C=\sqrt{[x^2+(D\sqrt{3}-y)^2+z^2]} \qquad C(7)$$

where $L_i$ is the range to the ith detector. This evaluation/testing procedure can be quickly calculated for a few sources by a pre-programmed portable computer.

Once the spatial coordinates of sources are known, the computed source locations may be set into a registered 3 dimensional ultrasound image of the volume of interest or standard imaging algorithms and techniques such as tomography may be applied.

Note that if the minimum linear resolution of a voxel is dx and the total linear dimension scanned is L, then the 3-detector transit time approach can determine a maximum of 3(L/dx) voxel sources, since this is the number of distinguishable simultaneous transit time equations available for three detectors. Then a 3 detector approach can image 300 voxel sources. In addition, by setting a higher threshold for signal detection, it is possible to reduce the number of contributing voxels.

C4. Cardiac and Vascular Applications

The EMAI technique can be applied whenever there are differences in conductivity between a target region or structure and its surroundings. Table 1 shows that blood has a much larger conductivity than other tissues. It is apparent, then, that EMAI can be used to non-invasively measure the extent of blood-containing cavities in the body, as well as the configurations of vascularized tissues.

One such application is the measurement of cardiac output (the volume of blood ejected from the heart in each pump cycle). This is an important quantity in the diagnosis of cardiovascular disease. Arterial distensibility and vascular resistance can be determined from diastolic and systolic blood pressure and pulse rate, providing the cardiac output is known. Currently there is no inexpensive non-invasive means of measuring cardiac output. By imaging the cardiac volume during a pump cycle, EMAI can be used to provide a simple non-invasive quantitative measure of this important parameter. Indeed, by measuring the variation of aorta and large artery volume during a cycle, information can also be obtained on the distensibility of the large arterial system.

Basic principles and experimental evidence have been presented showing that ultrasonic signals, of amplitude larger than random noise, would result from application of RF magnetic fields to objects containing compressible regions of electrical conductivity gradient. FDA limits for human applications can be satisfied while allowing for imaging of diagnostically useful tissue volumes in standard image acquisition times. Example imaging techniques have been proposed including those with direct application to breast imaging. An inexpensive three-detector system with variable threshold may be used for the purposes of characterizing lesions which have been previously detected or in the setting of a few sources which are well separated. Higher end systems such as lens/array systems can be used for volume imaging thus serving as an effective screening technique.

It is envisioned that the present invention may be used in conjunction with existing wavelet or other transform image processing algorithms including but not limited to image compression, noise reduction, edge detection, or singularity detection as a means of more accurately and efficiently constructing transforms of an image directly from data collected in use of the present invention without first reconstructing the image.

It is further envisioned that the present invention may be implemented in a format other than in software. Current and new technology development may, for example, make practical the layered deposition of integrated circuitry to automatically carry out the several processes of the disclosure of this invention.

Although the present invention is described with reference to the presently preferred embodiments, it is understood that the invention as defined by the claims is not limited to these described embodiments. Various other changes and modifications to the invention will be recognized by those skilled in this art and will still fall within the scope and spirit of the invention, as defined by the accompanying claims.

What is claimed is:

1. A method of locating conductivity gradients and discontinuities within a subject comprising:
   impinging a target site including conductivity gradients and discontinuities within a subject with pulsed RF electric fields;
   receiving ultrasound signals produced at said target site caused by said impinging of said target site with said pulsed RF electric fields;
   processing said ultrasound signals to quantitatively locate features of said conductivity gradients and discontinuities defined at said target site;
   computing one or more volumes bounded by features of opposite signs which are continuous;
   following changes in said volumes during cardiac cycles;
   noting any wavelike motion along said volumes; and
   computing liquid flow rate from said wavelike motion.

2. The method of claim 1, further comprising displaying tomographic and holographic images of said features.

3. The method of claim 1, wherein said receiving ultrasound signals produced at said target site comprises receiving ultrasound signals produced at said target site using an ultrasonic sensor or an array of ultrasonic sensors.

4. The method of claim 1, wherein said receiving ultrasound signals produced at said target site caused by said impinging of said target site with said pulsed RF electric fields comprises receiving ultrasound signals produced at said target site caused by said impinging of said target site with said pulsed RF electric fields at said RF.

5. The method of claim 1, wherein said receiving ultrasound signals produced at said target site caused by said impinging of said target site with said pulsed RF electric fields comprises electromagnetically sensing said pulsed RF fields as a time reference signal.

6. The method of claim 1, wherein said impinging a target site including conductivity gradients and discontinuities within a subject with pulsed RF electric fields comprises causing pulsed RF electrical currents to flow through one or more conductors near or in contact with said subject to induce said electric field.

7. The method of claim 1, further comprising providing a duration of said pulsed RF electric field at a time equal to a desired longitudinal resolution divided by the speed of sound within said subject.

8. The method of claim 7, wherein said longitudinal resolution can range from about 0.1 mm to about 100 mm.

9. The method of claim 1, wherein a longitudinal resolution is a function of a frequency resolution of a received spectrum at a detector element; said longitudinal resolution being in the range of about 0.1 mm to about 100 mm.

10. The method of claim 1, wherein receiving ultrasound signals produced at said target site caused by said impinging of said target site with said pulsed RF electric fields comprises minimizing acoustic velocity discontinuity at an interface between said subject's skin and a sensor element using a mixture of fluids or gels in contact with said subject's skin.

11. The method of claim 1, wherein said receiving ultrasound signals produced at said target site caused by said impinging of said target site with said pulsed RF electric fields further comprises positioning a converging acoustic lens between said target site and a sensor element or array of sensor elements to concentrate said ultrasound signal onto said sensors.

12. The method of claim 11, further comprising using a measure of the excitation pulse length and signal time delays to determine resolution along the lens axis, and lens optics to determine transverse resolution.

13. The method of claim 1, further comprising superposing processed ultrasound signals resulting from a plurality of said pulsed RF electric fields at the same times relative to time reference signals averaging out noise or interference signals relative to said processed ultrasound resulting from said pulsed RF electric fields to clarify said recording of said processed ultrasound signals.

14. The method of claim 1, further comprising determining spatial distribution of said conductivity gradients or discontinuities using Fourier optics interpretation of said processed ultrasound signals.

15. The method of claim 1, wherein said pulsed RF electric fields contain two distinct frequencies and wherein an ultrasonic transduction or amplification is tuned to a linear combination of said two distinct frequencies to clarify a recording of said ultrasound signals.

16. An apparatus for locating conductivity gradients and discontinuities within a subject comprising:
   means for impinging a target site including conductivity gradients and discontinuities within a subject with pulsed RF electric fields;
   means for receiving ultrasound signals produced at said target site caused by said impinging of said target site with said pulsed RF electric fields; and
   means for processing said ultrasound signals to quantitatively locate a feature of said conductivity gradients and discontinuities defined at said target site, wherein said means for impinging a target site with pulsed RF electric fields comprises an RF pulse generator including a capacitor connected to a discharge through a resistor and a coil, forming a resonant circuit wherein a damping time of said resonant circuit is equal to a desired pulse duration of said pulsed electric fields, and wherein said discharge is controlled by one or more electronically activated switches.

17. The apparatus of claim 16, wherein said capacitor is charged from a current source that is shorted to ground during said discharge.

18. The apparatus of claim 16, wherein said means for impinging said target site with said pulsed RF electric fields comprises a combination of a magnetic induction means and a direct ohmic or low reactance capacitive contact.

19. The apparatus of claim 16, further comprising:
   a concentrating acoustic lens disposed between a subject and an ultrasonic transducer or an array of ultrasonic transducers all immersed in a fluid or gel having acoustic velocity approximately that within said subject;
   an RF pulse generator of angular frequency greater $10^6$ radians per second and less than $10^8$ radians per second; and
   a configuration of conductors disposed to provide pulsed RF magnetic field excitation to parts of said subject, ultrasonic signal transducers and processors connected to receive signals from said ultrasonic signal transducers and send processed signals to a memory.

20. An apparatus for locating conductivity gradients and discontinuities within a subject comprising:
   means for impinging a target site including conductivity gradients and discontinuities within a subject with pulsed RF electric fields;
   means for receiving ultrasound signals produced at said target site caused by said impinging of said target site with said pulsed RF electric fields; and
   means for processing said ultrasound signals to quantitatively locate a feature of said conductivity gradients and discontinuities defined at said target site, wherein said means for receiving ultrasound signals produced at said target site caused by said impinging of said target site with said pulsed RF electric fields comprises:
   one or more acoustic lenses; and
   a sensor array positioned to receive ultrasonic signals focused from different depths within said target site and means for sensing and recording a changing of fluid pressure encapsulated within said one or more acoustic lens to focus voxels from said different depths onto sensor array elements.

21. A method of locating conductivity gradients and discontinuities within a subject comprising:
   impinging a target site including conductivity gradients and discontinuities within a subject with pulsed RF electric fields;
   sensing ultrasound pulse signals produced at a plurality of ultrasound sensors within acoustic range of said target site caused by said impinging of said target site with said pulsed RF electric fields using a plurality of sensor sources and including electromagnetically sensing said pulsed RF fields as a time reference signal; and
   computing time delays of said recorded arrival times from the coordinates of one to a plurality of said conductivity gradients and discontinuities using said time reference signal;
   assigning each of said plurality of sensor sources of said ultrasound pulse signals arbitrarily among sources compatible with any of said measured time delays of said ultrasound signals;
   calculating all measured transit times with said assignments;
   comparing said calculations with all said transit times; and
   changing said assignments until said calculated and measured transit times agree within a longitudinal resolution interval.

22. A method of detecting conductivity gradients and discontinuities within a subject comprising:
   generating an ultrasound image of a target site within a subject;
   generating an electromagnetic acoustic image;
   combining said ultrasound image and said electromagnetic acoustic image to create a first diagnostic image; and
   computing the quadrature component of said electromagnetic acoustic image relative to a phase of a separately detected time reference signal of said electromagnetic acoustic image delayed by half the round trip transit time of said ultrasound image thereby determining the gradient of permittivity at said electromagnetic acoustic image.

23. The method of claim 22, wherein said generating an electromagnetic acoustic image comprises:
   impinging said target site within a subject with pulsed RF electric fields;
   receiving ultrasound signals produced at said target site caused by said impinging of said target site with said pulsed RF electric fields; and
   processing said ultrasound signals to quantitatively locate features of said conductivity gradients and discontinuities defined at said target site.

* * * * *